United States Patent
Jha et al.

(10) Patent No.: US 10,000,582 B2
(45) Date of Patent: Jun. 19, 2018

(54) ETHYLSULFONATED HYALURONIC ACID BIOPOLYMERS AND METHODS OF USE THEREOF

(71) Applicant: The Regents of the University of California, Oakland, CA (US)

(72) Inventors: Amit K. Jha, Oakland, CA (US); Eda Isil Altiok, Berkeley, CA (US); Wesley M. Jackson, Albany, CA (US); Kevin E. Healy, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 189 days.

(21) Appl. No.: 14/780,447

(22) PCT Filed: Apr. 1, 2014

(86) PCT No.: PCT/US2014/032528
§ 371 (c)(1),
(2) Date: Sep. 25, 2015

(87) PCT Pub. No.: WO2014/165513
PCT Pub. Date: Oct. 9, 2014

(65) Prior Publication Data
US 2016/0053029 A1    Feb. 25, 2016

Related U.S. Application Data

(60) Provisional application No. 61/807,660, filed on Apr. 2, 2013.

(51) Int. Cl.
*C08B 37/08* (2006.01)
*A61K 35/30* (2015.01)
*A61K 35/34* (2015.01)
*A61K 35/36* (2015.01)
*A61K 35/545* (2015.01)
*C08L 5/08* (2006.01)
*A61K 9/48* (2006.01)

(52) U.S. Cl.
CPC ........ *C08B 37/0072* (2013.01); *A61K 9/4816* (2013.01); *A61K 35/30* (2013.01); *A61K 35/34* (2013.01); *A61K 35/36* (2013.01); *A61K 35/545* (2013.01); *C08L 5/08* (2013.01); *C12N 2533/80* (2013.01)

(58) Field of Classification Search
CPC ........ A61K 35/30; A61K 35/34; A61K 35/36; A61K 35/545; A61K 9/4816
See application file for complete search history.

(56) References Cited

U.S. PATENT DOCUMENTS

| | | | |
|---|---|---|---|
| 5,013,724 A | | 5/1991 | Petitou et al. |
| 5,652,014 A | * | 7/1997 | Galin ............ A61L 27/34 427/2.1 |
| 6,051,701 A | * | 4/2000 | Cialdi ............ A61K 31/737 536/118 |
| 6,288,043 B1 | * | 9/2001 | Spiro ............ A61K 27/20 424/423 |
| 6,339,074 B1 | | 1/2002 | Cialdi et al. |
| 2009/0197797 A1 | | 8/2009 | Norbedo et al. |
| 2010/0278877 A1 | | 11/2010 | Tamura et al. |
| 2011/0046038 A1 | | 2/2011 | Healy et al. |

FOREIGN PATENT DOCUMENTS

WO    WO 2009/120893    10/2009

OTHER PUBLICATIONS

Abatangelo et al.; "Biocompatiblity and Enzymatic Degradation Studies on Sulphated Hyaluronic Acid Derivatives"; Biomaterials 18:1411, 1997.
Barbucci et al.; "Sulfated Hyaluronic Acid as Heparin-like Material: Physiochemical and Biological Characterization"; Journal of Materials Science: Materials in Medicine. 5 (11): 830-833, 1994.
Burdick, et al.; "Hyaluronic Acid Hydrogels for Biomedical Applications"; Adv Mater. Mar. 25, 2011;23(12):H41-56.
Cen et al.; "Assessment of in Vitro Bioactivity of Hyaluronic Acid and Sulfated Hyaluronic Acid Functionalized Electroactive Polymer"; Biomacromolecules. 5 (6): 2238-2246, 2004.
Necas et al.; "Hyaluronic Acid (Hyaluronan): A Review"; Veterinarni Medicina, 53 (8): 397-411, 2008.
Prestwich; "Hyaluronic Acid-Based Clinical Biomaterials Derived for Cell and Molecule Delivery in Regenerative Medicine"; Journal of Controlled Release. 155 (2): 193-199, 2011.

* cited by examiner

*Primary Examiner* — Alma Pipic
(74) *Attorney, Agent, or Firm* — Bozicevic Field & Francis, LLP; Paula A. Borden

(57) ABSTRACT

The present disclosure provides methods for sulfonation of hyaluronic acid. The present disclosure provides sulfonated hyaluronic acid, and compositions, including pharmaceutical compositions, comprising the sulfonated hyaluronic acid. The present disclosure provides implantable materials and drug delivery compositions comprising a subject sulfonated hyaluronic acid.

17 Claims, 15 Drawing Sheets

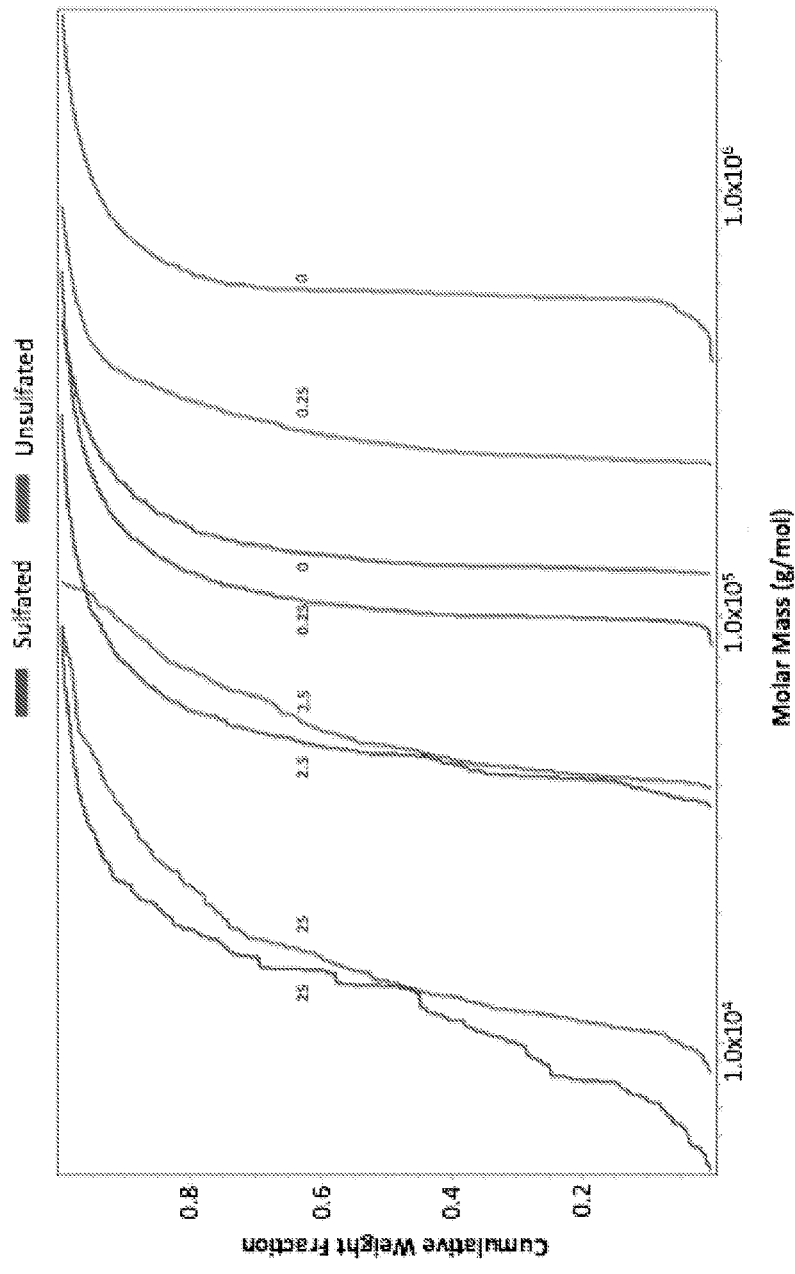
Figure 1A: HyA and ES-HyA Degradation
HyA and ES-HyA at 3mg/ml was subjected to hyaluronidase degradation for 6 hours at 37°C. Samples were then analyzed with SEC-MALS for analysis of molecular weight distributions

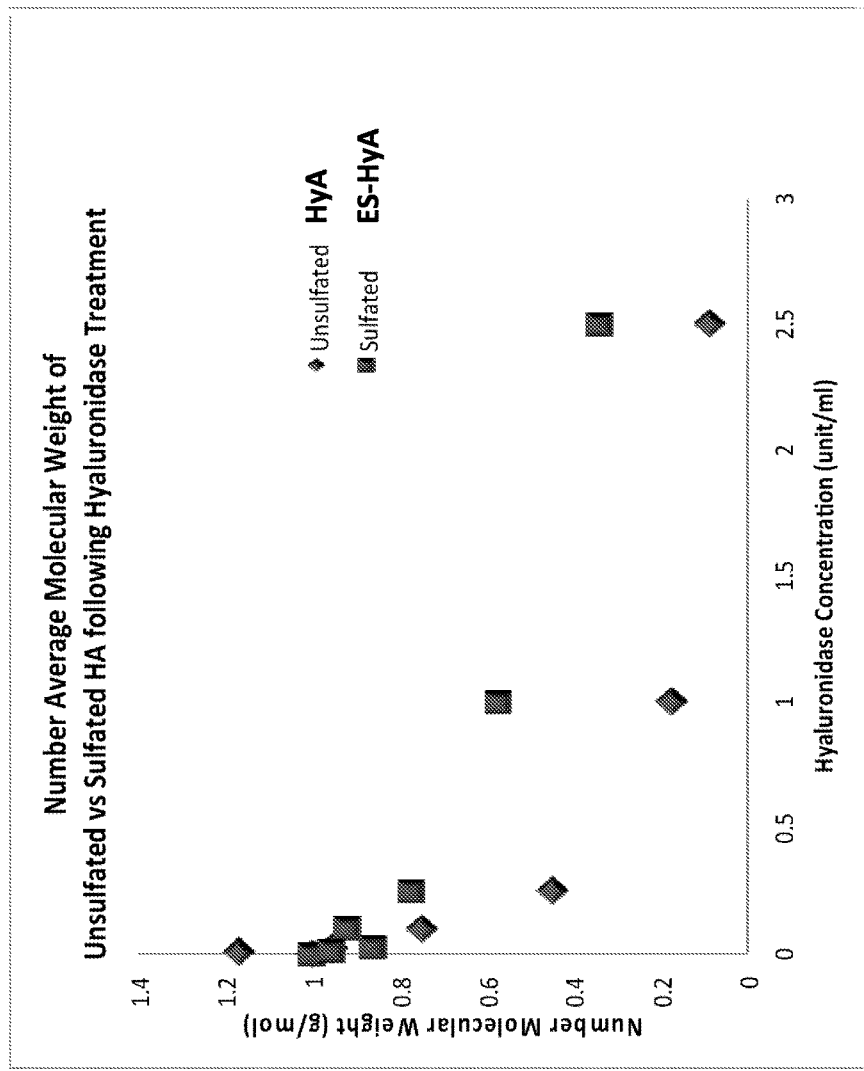
Figure 1B. Results of the SEC-MALS degradation study were normalized to 1 to reflect differences in degradation profiles with and without sulfation.

Fig 2: Combustion Analysis

| Catalyst | % Found Unsulfated | % Found Sulfated |
|---|---|---|
| C | 35.57 | 35.98 |
| H | 5.44 | 5.8 |
| N | 3.03 | 3.14 |
| S | 0.27 | 0.5 |

HyA (unsulfated) and ES-HyA (sulfated) was analyzed with combustion analysis for carbon, hydrogen, nitrogen and sulfur content.

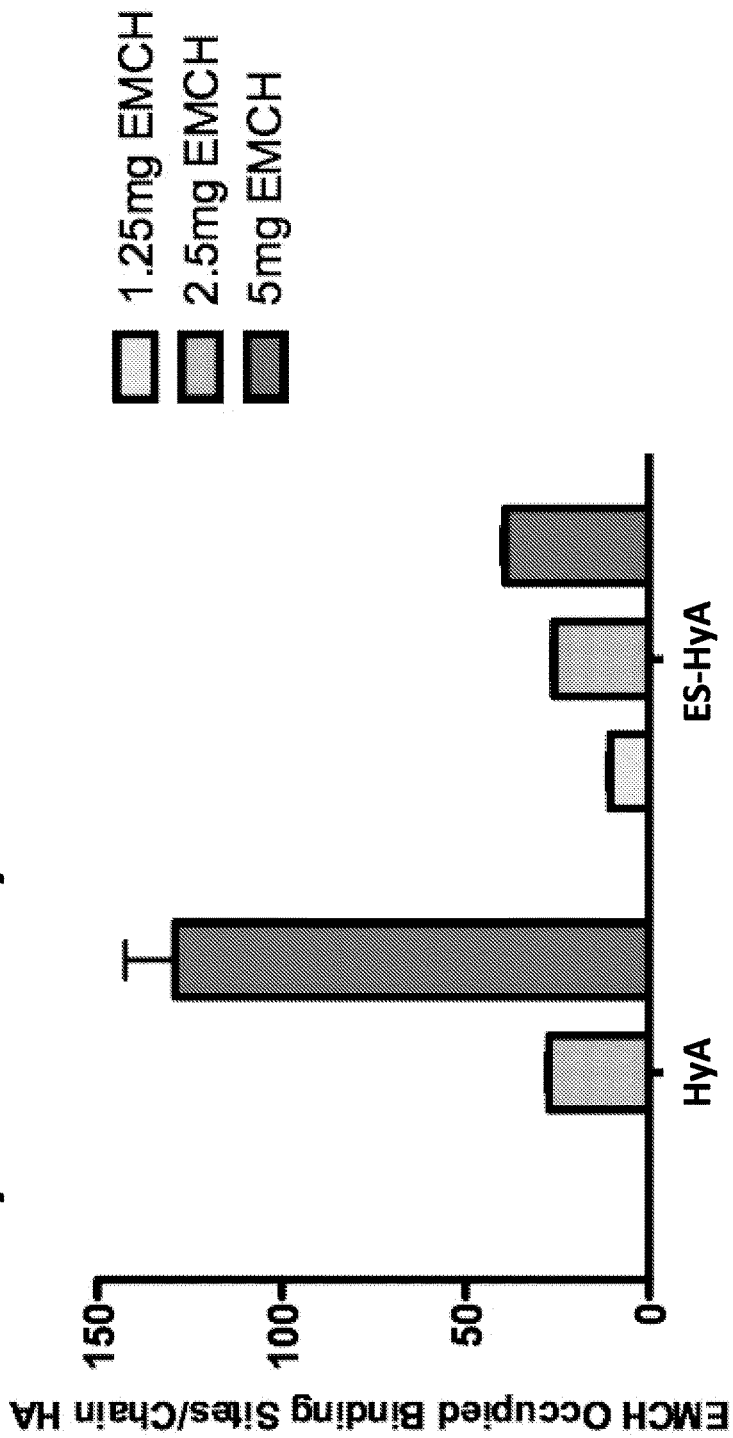

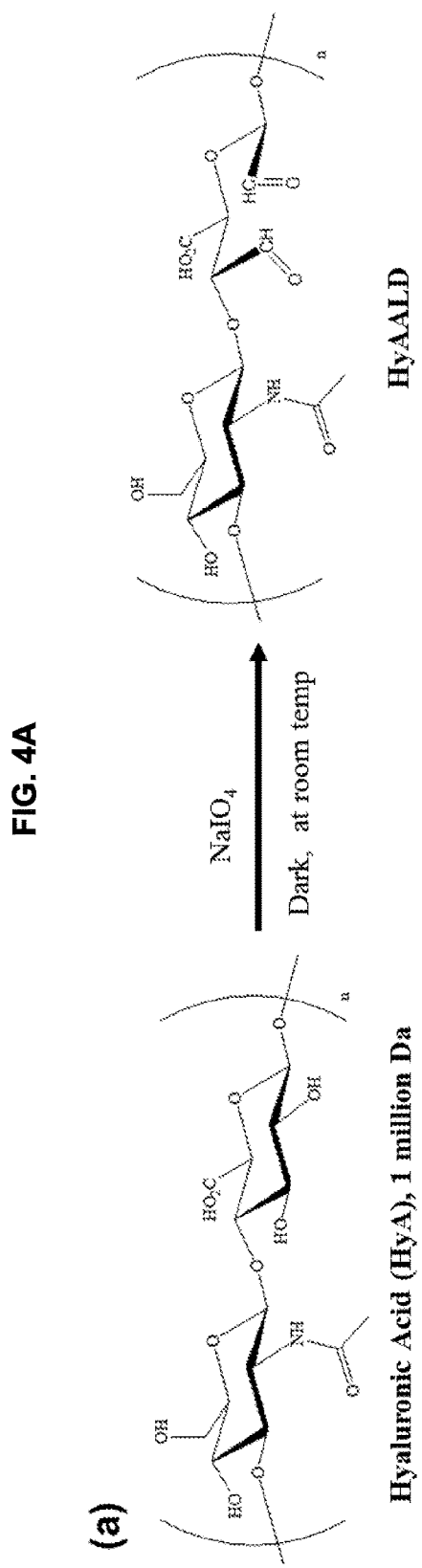

ETHYLSULFONATED HYALURONIC ACID BIOPOLYMERS AND METHODS OF USE THEREOF

CROSS-REFERENCE

This application claims the benefit of U.S. Provisional Patent Application No. 61/807,660, filed Apr. 2, 2013, which application is incorporated herein by reference in its entirety.

INTRODUCTION

Hyaluronic acid (HyA) is a natural glycosaminoglycan (GAG) biopolymer with a variety of favorable biological properties, such as promoting cell growth, inhibiting thrombosis and modulating the tissue distribution of secreted growth factors. It is currently used in a variety of products to improve surface biocompatibility, as a substrate for tissue engineering and to control drug pharmacodynamics. A significant limiting factor for the use of HyA in medical applications is its degradation in vivo due to the high endogenous concentration of hyaluronidase and other glycolytic proteins. Depending on the tissue, the half-life of HyA can be as short as minutes, and when in contact with the blood, its half-life is approximately 1.5 hours. Therefore, current uses of HyA are limited to applications where its biomaterial properties are only required for a short duration of time.

Sulfation is a natural means of preserving GAG biopolymers. In vivo, enzymes replace the native hydroxyl groups on the GAG disaccharide unit with sulfates, and as a result, the biopolymer resists the activity of glycolytic proteins. Two commonly sulfated GAGs include heparin sulfate and chondroitin sulfate. Both of these compounds are used in medical applications to take advantage of their enhanced stability. However, typical high-end molecular weights for heparin sulfate and chondroitin sulfate are typically in the range of 30 kDa and 150 kDa, respectively. The potential uses for the sulfated GAG biopolymers are therefore limited in comparison to HyA, which is routinely synthesized with molecular weights exceeding 1.0 MDa. However, Hya is the only GAG that does not become sulfated naturally.

To improve the stability of HyA in vivo there are several methods of synthetic GAG sulfation. However, the primary drawback to current sulfation methods is that the chemical reactions must be performed in organic solvents that significantly complicate the process of translating the final product into a biocompatible formulation. Furthermore, a high degree of sulfation (substitution ratios of 2-4 sulfates per disaccharide unit) is required to satisfactorily resist enzymatic degradation. Thus, extensive modification of the HyA molecule limits the ability to perform additional chemical reactions on the biopolymer to improve its utility.

There is a need in the art for methods of increasing the in vivo half-life of hyaluronic acid.

LITERATURE

U.S. Pat. No. 6,338,074; U.S. Pat. No. 5,013,724; Abatangelo et al. (1997) *Biomaterials* 18:1411; Barbucci et al. (1994) Journal of Materials Science: Materials in Medicine. 5:830; Necas et al (2008) *Veterinarni Medicina*, 53(8): 397

SUMMARY

The present disclosure provides methods for sulfonation of hyaluronic acid. The present disclosure provides sulfonated hyaluronic acid, and compositions, including pharmaceutical compositions, comprising the sulfonated hyaluronic acid. The present disclosure provides implantable materials and drug delivery compositions comprising a subject sulfonated hyaluronic acid.

BRIEF DESCRIPTION OF THE DRAWINGS

FIG. 1A depicts HyA and ES-HyA degradation.

FIG. 1B depicts average molecular weight of unsulfated versus sulfated HyA following hyaluronidase treatment.

FIG. 2 depicts combustion analysis of unsulfated HyA and sulfated HyA.

FIG. 3 depicts efficiency of EMCH conjugation to unsulfated HyA and sulfated HyA (ES-HyA).

FIGS. 4A-B depict the synthesis of sulfated hyaluronic acid.

DEFINITIONS

Figure 4B:
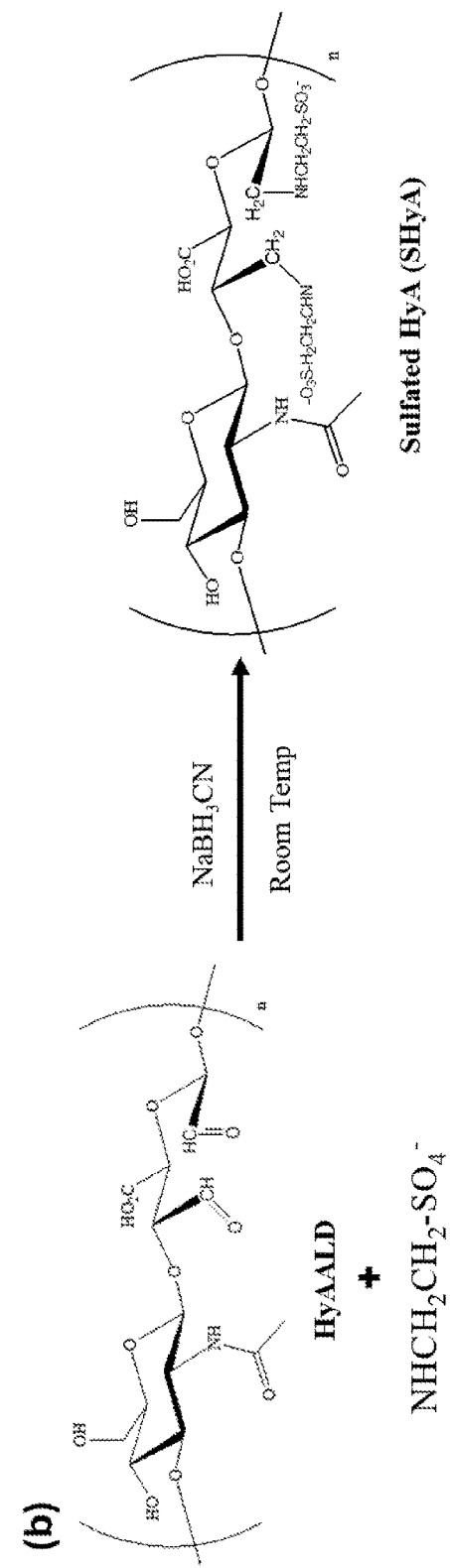

The terms "subject," "individual," "host," and "patient" are used interchangeably herein to a member or members of any mammalian or non-mammalian species. Subjects and patients thus include, without limitation, humans, non-human primates, canines, felines, ungulates (e.g., equine, bovine, swine (e.g., pig)), avians, rodents (e.g., rats, mice), and other subjects. Non-human animal models, particularly mammals, e.g. a non-human primate, a murine (e.g., a mouse, a rat), lagomorpha, etc. may be used for experimental investigations.

"Treating" or "treatment" of a condition or disease includes: (1) preventing at least one symptom of the condition, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient, in combination with another agent, or alone in one or more doses, to effect such treatment for the disease. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, the term "label moiety" is intended to mean one or more atoms that can be specifically detected to indicate the presence of a substance to which the one or more atom is attached. A label moiety can be a primary label that is directly detectable or secondary label that can be indirectly detected, for example, via interaction with a primary label. Exemplary primary labels include, without limitation, an isotopic label such as a naturally non-abundant heavy isotope or radioactive isotope, examples of which include $^{14}C$, $^{123}I$, $^{124}I$, $^{125}I$, $^{131}I$, $^{32}P$, $^{35}S$ or $^{3}H$; optically detectable moieties such as a chromophore, luminophore, fluorophore, quantum dot or nanoparticle; electromagnetic spin label; calorimetric agent; magnetic substance; electron-rich material such as a metal; electrochemiluminescent label such as $Ru(bpy)_3^{2+}$; moiety that can be detected based on a nuclear magnetic, paramagnetic, electrical, charge to mass, or thermal characteristic; or light scattering or plasmon resonant materials such as gold or silver particles. Fluorophores that are useful in the invention include, for example, fluorescent lanthanide complexes, including those of Europium and Terbium, fluorescein, fluorescein isothiocyanate, carboxyfluorescein (FAM), dichlorotriazinylamine fluorescein, rhodamine, tetramethylrhodamine, umbelliferone, eosin, erythrosin, coumarin, methyl-coumarins, pyrene, Malacite green, Cy3, Cy5, stilbene, Lucifer Yellow, Cascade Blue™, Texas Red, alexa dyes, dansyl chloride, phycoerythin, green fluorescent protein and its wavelength shifted variants, bodipy, and others known in the art such as those described in Haugland, Molecular Probes Handbook, (Eugene, Oreg.) 6th Edition; The Synthegen catalog (Houston, Tex.), Lakowicz, Principles of Fluorescence Spectroscopy, 2nd Ed., Plenum Press New York (1999), or WO 98/59066.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a sulfonated hyaluronic acid matrix" includes a plurality of such matrices and reference to "the composition" includes reference to one or more compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods for sulfonation of hyaluronic acid. The present disclosure provides sulfonated hyaluronic acid, and compositions, including pharmaceutical compositions, comprising the sulfonated hyaluronic acid. The present disclosure provides implantable materials and drug delivery compositions comprising a subject sulfonated hyaluronic acid.

Methods for Sulfonation of Hyaluronic Acid

In certain embodiments, a method for sulfonation of hyaluronic acid is provided. Hyaluronic acid is a polymer of disaccharides, themselves composed of D-glucuronic acid and D-N-acetylglucosamine, linked via alternating β-1,4 and β-1,3 glycosidic bonds.

In certain embodiments, the method includes activating one or more carbonyl groups in a hyaluronic acid polymer. Activating the carbonyl group may produce an activated carbonyl group in the hyaluronic acid polymer.

Activating the carbonyl group in the hyaluronic acid polymer may be accomplished using a variety of methods. For example, in some embodiments, the activating includes coupling a coupling agent to the carbonyl group to produce a coupling agent-modified hyaluronic acid polymer. As such, the activated carbonyl group may include a carbonyl group of the hyaluronic acid polymer attached (e.g., bonded, such as covalently bonded) to the coupling agent. The coupling agent can be any of a variety of coupling agents that provide for attachment of the coupling agent to the carbonyl group of the hyaluronic acid polymer. For instances, the coupling agent may provide for attachment to a carbonyl group, such as a carboxyl group or an aldehyde group. In certain instances, the coupling agent is configured for attachment to a carboxyl group in the hyaluronic acid polymer. In these instances, the coupling agent may include a moiety that is reactive towards a carbonyl group, such as a carboxyl-reactive moiety. For example, the coupling agent may include adipic acid dihydrazide.

In certain embodiments, the method further includes attaching a sulfonate-containing moiety to the activated carbonyl group to produce a sulfonated hyaluronic acid polymer. As discussed above, coupling the coupling group to a carbonyl group of the hyaluronic acid polymer may produce a coupling agent-modified hyaluronic acid polymer. In these embodiments, attaching the sulfonate-containing moiety to the activated carbonyl group includes attaching the sulfonate-containing moiety to the coupling agent-modified hyaluronic acid polymer to produce the sulfonated hyaluronic acid polymer. As such, the sulfonate-containing moiety is indirectly coupled to the carbonyl group of the hyaluronic acid polymer through the coupling agent. For instance, one end of the coupling agent may be attached to the hyaluronic acid polymer, as described above in the first step of the presently disclosed method. The other end of the coupling agent may be attached to the sulfonate-containing moiety, as described in the second step of the presently disclosed method.

In other embodiments, the first step of the method, activating the carbonyl group in the hyaluronic acid polymer, includes producing at least one reactive carbonyl group on the hyaluronic acid polymer. For instance, the reactive carbonyl group may include a reactive aldehyde group. In some instances, the reactive carbonyl group may be produced on one or both of the saccharides that make up the disaccharide units of hyaluronic acid. For example, the reactive carbonyl groups may be produced on one or more of the D-glucuronic acid subunits of hyaluronic acid, or may be produced on one or more of the D-N-acetylglucosamine subunits of hyaluronic acid. In certain embodiments, the reactive carbonyl groups are produced on the D-glucuronic acid subunits of hyaluronic acid. In these instances, the reactive carbonyl groups (e.g., reactive aldehyde groups) may be produced by cleavage of the D-glucuronic acid ring. For example, vicinal diols of the D-glucuronic acid ring may be cleaved to form two aldehyde groups from the D-glucuronic acid subunit of hyaluronic acid.

Cleavage of vicinal diols may be may be accomplished using a variety of methods. For example, in some embodiments, the methods of cleaving vicinal diols includes sodium periodate oxidation. In certain embodiments sodium periodate oxidation of vicinal diols is achieved by introducing sodium periodate to a reaction mixture that contains vicinal diols. Sodium periodate oxidation be accomplished using a variety of reaction conditions. For example, in some embodiments, sodium periodate oxidation is performed at room temperature and the reaction is protected from light, e.g., performed in the dark. In some instances, reaction conditions are modified in order to increase or reduce the production of reactive carbonyl groups produced by a particular sodium periodate oxidation reaction. Those of skill in the art will understand that reaction conditions for sodium periodate oxidation may be modified in order to optimize reaction output, reaction convenience, or any other reaction parameter of interest.

The reactive carbonyl groups (e.g., reactive aldehyde groups) may then be coupled to the sulfonate-containing moiety to produce the sulfonated hyaluronic acid polymer. As such, the method may include the step where the attaching includes coupling the sulfonate-containing moiety to the reactive carbonyl group to produce the sulfonated hyaluronic acid polymer. In these embodiments, the sulfonate-containing moiety may be coupled directly to the hyaluronic acid polymer without an intervening coupling group.

Coupling of the sulfonate-containing moiety to the reactive carbonyl group to produce the sulfonated hyaluronic acid polymer may be accomplished using a variety of methods. For example, in some embodiments an aldehyde derivative of hyaluronic acid is first produced by methods described herein and reactive carbonyl groups of the aldehyde derivative of hyaluronic acid are coupled to sulfonate-containing moieties. In some embodiments, the coupled molecule is further reduced after coupling by a reducing agent. Any convenient reducing agent useful in reducing the coupled molecule to produce a sulfonated hyaluronic acid polymer may be used. For example, in some embodiments the reducing agent may be a mild reducing agent, e.g., sodium cynoborohydride.

In certain embodiments, the method is performed in an aqueous reaction mixture. By "aqueous" is meant a solution or mixture where the primary solvent is water. In certain instances, an aqueous reaction mixture may facilitate the production of a sulfonated hyaluronic acid polymer in a pharmaceutically acceptable solution. In certain embodiments, the aqueous reaction mixture has a pharmaceutically acceptable pH. For example, the reaction mixture may have a pH of 5 to 7.

In certain embodiments, the method finds use in the production of a sulfonated hyaluronic acid polymer with a high molecular weight. For example, the hyaluronic acid polymer may have a molecular weight of 100 kDa or more, such as 200 kDa or more, including 300 kDa or more, or 400 kDa or more, or 500 kDa or more, or 600 kDa or more, or 700 kDa or more, or 800 kDa or more, or 900 kDa or more, or 1 MDa or more, or 1.5 MDa or more. In some instances, the hyaluronic acid has a molecular weight of 400 kDa or more. In some instances, the hyaluronic acid polymer has a molecular weight of 1 MDa or more.

In certain embodiments, the method is performed at a temperature ranging from 10° C. to 40° C., such as from 15° C. to 35° C., or from 15° C., to 30° C., or from 15° C. to 25° C. In certain embodiments, the method is performed at room temperature, e.g., standard room temperature, such as about 20° C.

In certain embodiments, the sulfonated hyaluronic acid polymer has a particular sulfonate:disaccharide ratio. By "sulfonate:disaccharide ratio is meant the average number of sulfonate groups per disaccharide units of the sulfonated hyaluronic acid polymer. For example, a sulfonate:disaccharide ratio of 1 indicates that there are, on average, one sulfonate groups per disaccharide units in the sulfonated hyaluronic acid polymer. By "average" is meant the arithmetic mean. In certain instances, the sulfonated hyaluronic acid polymer has a sulfonate:disaccharide ratio of 2 or less, such as 1.7 or less, or 1.5 or less, or 1.3 or less, or 1 or less, such as 0.9 or less, or 0.8 or less, or 0.7 or less, or 0.6 or less, or 0.5 or less, or 0.4 or less, or 0.3 or less, or 0.2 or less, or 0.1 or less. In some instances, the sulfonated hyaluronic acid polymer has a sulfonate:disaccharide ratio of 1 or less. In some instances, the sulfonated hyaluronic acid polymer has a sulfonate:disaccharide ratio of 0.5 or less. In some instances, the sulfonated hyaluronic acid polymer has a sulfonate:disaccharide ratio of 0.1 or less.

In certain embodiments, the sulfonate-containing moiety includes a reactive group and a sulfonate group. The reactive group may be any convenient reactive group that provides from reaction (e.g., coupling reaction) between the sulfonate-containing moiety and the coupling agent (e.g., the coupling agent coupled to the hyaluronic acid polymer) or the reactive carbonyl group of the hyaluronic acid polymer as described above. For example, as described above, the coupling agent may include a hydrazide reactive group. In these instances, the sulfonate-containing moiety may include a reactive group (e.g., a reactive group that reacts with a hydrazide group), such as an aldehyde group. For instance, the sulfonate-containing moiety may include 3-oxopropane-1-sulfonate. In other embodiments, as described above, the method may include producing a reactive carbonyl group on the hyaluronic acid polymer, such as a reactive aldehyde group. In these embodiments, the reactive group of the sulfonate-containing moiety may be configured to react with the reactive carbonyl group (e.g., reactive aldehyde group) of the hyaluronic acid polymer. For instance, the sulfonate-containing moiety may include an amino group. In these instances, examples of the sulfonate-containing moiety may include 2-aminoethanesulfonate or 2-aminoethyl hydrogen sulfate.

In certain embodiments, the sulfonated hyaluronic acid polymer has a degradation half-life significantly longer that an un-sulfonated hyaluronic acid polymer. By degradation half-life is meant the time in which it takes half of the sulfonated hyaluronic acid polymer to degrade. For example, the sulfonated hyaluronic acid polymer may have an in vivo half-life of 5 hours or more, such as 6 hours or more, or 7 hours or more, or 8 hours or more, or 9 hours or more, or 10 hours or more, or 12 hours or more, or 15 hours or more, or 17 hours or more, or 20 hours or more, or 22 hours or more, or 24 hours or more, or 25 hours or more, or 27 hours or more, or 30 hours or more, or 35 hours or more, or 40 hours or more, or 45 hours or more, or 48 hours or more. In some instances, the sulfonated hyaluronic acid polymer has an in vivo half-life of 10 hours or more.

In certain embodiments, the method further includes conjugating the sulfonated hyaluronic acid polymer to one or more moieties of interest. For example, embodiments of the sulfonated hyaluronic acid may have a low sulfonate:disaccharide ratio as described above. In these embodiments, there may be a plurality of unmodified disaccharide units in the hyaluronic acid polymer. In some instances, these unmodified disaccharide units may be able to participate in conjugation reactions with other functionalized moieties of interest. Moieties of interest include, but are not limited to, crosslinkers, proteins, peptides, labels (e.g., dyes, fluorescent labels, etc.), drugs, and the like.

Sulfonated Hyaluronic Acid

Embodiments of the present disclosure further include a sulfonated hyaluronic acid polymer produced by the methods described herein. Embodiments of the present disclosure include a sulfonated hyaluronic acid matrix (a "sulfonated HyA matrix"). A subject sulfonated HyA matrix comprises a sulfonated HyA polymer, as discussed above, and has the properties discussed above.

In certain instances, the sulfonated hyaluronic acid polymer has a sulfonate:disaccharide ratio of 2 or less, such as 1.7 or less, or 1.5 or less, or 1.3 or less, or 1 or less, such as 0.9 or less, or 0.8 or less, or 0.7 or less, or 0.6 or less, or 0.5 or less, or 0.4 or less, or 0.3 or less, or 0.2 or less, or 0.1 or less. In some instances, the sulfonated hyaluronic acid polymer has a sulfonate:disaccharide ratio of 1 or less. In some instances, the sulfonated hyaluronic acid polymer has a sulfonate:disaccharide ratio of 0.5 or less. In some instances, the sulfonated hyaluronic acid polymer has a sulfonate:disaccharide ratio of 0.1 or less.

In certain embodiments, the sulfonated hyaluronic acid polymer has a degradation half-life significantly longer that an un-sulfonated hyaluronic acid polymer. By degradation half-life is meant the time in which it takes half of the sulfonated hyaluronic acid polymer to degrade. For example, the sulfonated hyaluronic acid polymer may have a half-life of 5 hours or more, such as 6 hours or more, or 7 hours or more, or 8 hours or more, or 9 hours or more, or 10 hours or more, or 12 hours or more, or 15 hours or more, or 17 hours or more, or 20 hours or more, or 22 hours or more, or 24 hours or more, or 25 hours or more, or 27 hours or more, or 30 hours or more, or 35 hours or more, or 40 hours or more, or 45 hours or more, or 48 hours or more. In some instances, the sulfonated hyaluronic acid polymer has an in vivo half-life of 10 hours or more.

A subject sulfonated hyaluronic acid polymer can further include one or more additional moieties, e.g., crosslinkers, proteins, peptides, labels (e.g., dyes, fluorescent labels, etc.), drugs, and the like.

Embodiments of the present disclosure further include a pharmaceutical composition that includes a sulfonated hyaluronic acid polymer as described herein. The pharmaceutical compositions may also include a pharmaceutically acceptable buffer. The pharmaceutical compositions may also include one or more of an excipient, solubilizer, stabilizer, buffer, tonicity modifier, bulking agent, viscosity enhancer/reducer, surfactant, chelating agent, adjuvant, combinations thereof, and the like.

As noted above, a subject sulfonated hyaluronic acid polymer can further include one or more additional moieties, e.g., crosslinkers, polypeptides, labels (e.g., dyes, fluorescent labels, etc.), drugs, and the like. Such moieties can be conjugated to the sulfonated hyaluronic acid polymer, to form a sulfonated hyaluronic acid polymer conjugate.

Polypeptides that are of interest for attachment to a sulfonated hyaluronic acid polymer, to generate a subject polypeptide-polymer conjugate include, e.g., growth factors, receptors, polypeptide ligands for receptors, enzymes, antibodies, coagulation factors, anti-coagulation factors, angiogenic factors, anti-angiogenic factors, etc. Suitable polypeptides include linear polypeptides and cyclic polypeptides. Suitable polypeptides include naturally occurring polypeptides, synthetic polypeptides, and the like. Polypeptides that are of interest for attachment to a sulfonated hyaluronic acid polymer, to generate a subject polypeptide-polymer conjugate include polypeptides having a molecular weight of from about 1 kDa to about 2000 kDa, e.g., from about 1 kDa to about 2 kDa, from about 2 kDa to about 2.5 kDa, from about 2.5 kDa to about 5 kDa, from about 5 kDa to about 10 kDa, from about 10 kDa to about 25 kDa, from about 25 kDa to about 50 kDa, from about 50 kDa to about 100 kDa, from about 100 kDa to about 250 kDa, from about 250 kDa to about 500 kDa, from about 500 kDa to about 1000 kDa, from about 1000 kDa to about 2000 kDa. In some cases, the polypeptide has a molecular weight greater than 2000 kDa.

Suitable polypeptides include, but are not limited to, an interferon (e.g., IFN-γ, IFN-α, IFN-β, IFN-ω; IFN-τ); an insulin (e.g., Novolin, Humulin, Humalog, Lantus, Ultralente, etc.); an erythropoietin ("EPO"; e.g., Procrit®, Eprex®, or Epogen® (epoetin-α); Aranesp® (darbepoietin-α); NeoRecormon®, Epogin® (epoetin-β) and the like); an antibody (e.g., a monoclonal antibody) (e.g., Rituxan® (rituximab); Remicade® (infliximab); Herceptin® (trastuzumab); Humira™ (adalimumab); Xolair® (omalizumab); Bexxar® (tositumomab); Raptiva™ (efalizumab); Erbitux™ (cetuximab); and the like), including an antigen-binding fragment of a monoclonal antibody; a blood factor (e.g., Activase® (alteplase) tissue plasminogen activator; NovoSeven® (recombinant human factor VIIa); Factor VIIa; Factor VIII (e.g., Kogenate®); Factor IX; β-globin; hemoglobin; and the like); a colony stimulating factor (e.g., Neupogen® (filgrastim; G-CSF); Neulasta (pegfilgrastim); granulocyte colony stimulating factor (G-CSF), granulocyte-monocyte colony stimulating factor, macrophage colony stimulating factor, megakaryocyte colony stimulating factor; and the like); a growth hormone (e.g., a somatotropin, e.g., Genotropin®, Nutropin®, Norditropin®, Saizen®, Serostim®, Humatrope®, etc.; a human growth hormone; and the like); an interleukin (e.g., IL-1; IL-2, including, e.g., Proleukin®; IL-3, IL-4, IL-5, IL-6, IL-7, IL-8, IL-9; etc.); a growth factor (e.g., Regranex® (becapermin; PDGF); Fiblast® (trafermin; bFGF); Stemgen® (ancestim; stem cell factor); keratinocyte growth factor; an acidic fibroblast growth factor, a stem cell factor, a basic fibroblast growth factor, a hepatocyte growth factor; and the like); a receptor (e.g., a TNF-α-binding soluble receptor such as Enbrel® (etanercept); a VEGF receptor; a interleukin receptor; a γ/δ T cell receptor; and the like); a neurotransmitter receptor (e.g., a nicotinic acetylcholine receptor, a glutamate receptor, a GABA receptor, etc.); an enzyme (e.g., α-glucosidase; Cerazyme® (imiglucarase; β-glucocerebrosidase, Ceredase® (alglucerase); an enzyme activator (e.g., tissue plasminogen activator); a chemokine (e.g., IP-10; Mig; Groα/IL-8, RANTES; MIP-1α; MIP-1β; MCP-1; PF-4; and the like); an angiogenic agent (e.g., vascular endothelial growth factor (VEGF); an anti-angiogenic agent (e.g., a VEGF receptor); a neuroactive peptide such as bradykinin, cholecystokinin, gastin, secretin, oxytocin, gonadotropin-releasing hormone, beta-endorphin, enkephalin, substance P, somatostatin, prolactin, galanin, growth hormone-releasing hormone, bombesin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, an insulin-like growth factor, a luteinizing hormone, a macrophage activating factor, tumor necrosis factor, a neutrophil chemotactic factor, a nerve growth factor a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); an ion channel, e.g., cystic fibrosis transmembrane conductance regulator (CFTR); dystrophin; utrophin, a tumor suppressor; lysosomal enzyme acid α-glucosidase (GAA); and the like.

Suitable polypeptides include sonic hedgehog (Shh), bone morphogenic protein-4, interleukin-3 (IL-3), stem cell factor-1 (SCF-1), fms-like tyrosine kinase-3 (Flt3) ligand, leukemia inhibitory factor (LIF), fibroblast growth factor-2 (FGF-2), and epidermal growth factor (EGF). Suitable polypeptides include brain-derived neurotrophic factor (BDNF), nerve growth factor (NGF), neurotrophin-3 (NT-3), neurotrophin-4 (NT-4), neurotrophin-5 (NT-5), basic fibroblast growth factor (bFGF), insulin-like growth factor-1 (IGF-1), glial-derived neurotrophic factor (GDNF), and protease nexin-1. Suitable angiogenic polypeptides include a netrin-1 polypeptide, a vascular endothelial growth factor (VEGF) polypeptide, a platelet-derived growth factor (PDGF) polypeptide, a fibroblast growth factor (FGF) polypeptide, and an angiopoietin polypeptide.

Suitable polypeptides also include clotting factors, e.g., thrombin, etc. Suitable polypeptides also include anti-coagulants. Suitable polypeptides also include cell-binding polypeptides.

Suitable polypeptides also include, e.g., Nestin, Vimentin, Prominin/CD133, Sonic hedgehog and other hedgehog ligands, Wnt ligands, Neurocan/tenascin C, Nurr 1, Pax-6, Sox-2, Musashi-1, NG2/CSPG-4, Neuro D3, Neurogenin 1, and active fragments and subsequences of any these polypeptides.

Suitable polypeptides also include, e.g., β tubulin III, MAP2, Neuron specific enolase, NCAM, CD24, HAS, Synapsin I, Synaptophysin, CAMK IIa, Tyrosine hydroxylase, Glutamate transporter, Glutamate receptor, Choline rececptor, nicotinic A2, EphB2, GABA-A receptor, Serotonin (5HT-3) receptor, Choline acetyltransferase, and fragments and subsequences of any of the foregoing.

Suitable polypeptides also include, e.g., a calcium channel; a T-cell antigen receptor; a chemokine receptor; a potassium channel; a neurotransmitter receptor (e.g., a serotonin receptor; a GABA receptor; a glutamate receptor; a nicotinic acetylcholine receptor; etc.); a growth factor receptor (e.g., epidermal growth factor receptor; vascular endothelial growth factor receptor, etc.); a bone morphogenetic protein; a polypeptide that activates a cell signaling pathway; an antibody; and the like.

Suitable drugs include, but are not limited to, cytotoxic compounds (e.g., cancer chemotherapeutic compounds); antiviral compounds; biological response modifiers (e.g., hormones, chemokines, cytokines, interleukins, etc.); microtubule affecting agents; hormone modulators; steroidal compounds; and the like. Suitable drugs include those listed hereinbelow (e.g., lipid-regulating agents; sex hormones; androgenic agents; antihypertensive agents; anti-diabetic agents; anti-viral agents, as described below). Suitable drugs include cancer chemotherapeutic agents.

Suitable antibodies (e.g., for use in cancer treatment) include, but are not limited to, naked antibodies, e.g., trastuzumab (Herceptin), bevacizumab (Avastin™), cetuximab (Erbitux™) panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), $^{90}$Y-labelled ibritumomab tiuxetan (Zevalin™), $^{131}$I-labelled tositumoma (Bexxar™), etc. Suitable antibodies for use in cancer treatment include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), Le$^y$, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP, Tenascin, etc.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); taxanes (including taxane derivatives); etc.

Utility

Sulfonated hyaluronic acid as described above can be used in a variety of medical applications. Such applications include, e.g., tissue engineering and drug delivery. As such, the present disclosure provides artificial tissues and drug delivery compositions comprising a subject sulfonated hyaluronic acid.

For use in a medical application, such as tissue engineering and drug delivery, a subject sulfonated hyaluronic acid (also referred to herein as "ethylsulfonated hyaluronic acid" or "ES-HyA") can be used without further modification. Alternatively, a subject ES-HyA can be further modified to include 1, 2, 3, or more different moieties covalently or non-covalently linked to the hyaluronic acid (HyA) core.

Implantable ES-HyA Material and Tissue Engineering

The present disclosure provides artificial tissue, e.g., an implantable polymeric material, comprising a subject ES-HyA matrix. A subject implantable ES-HyA material can form a two-dimensional or a three-dimensional structure. A subject implantable ES-HyA material can form a variety of structures, including, but not limited to, surgical suture and ligature strands; scaffolds and patches for soft and hard tissue regeneration; guided bone regeneration (GBR); guided tissue regeneration (GTR); surgical meshes; gauze for wound dressing; artificial organs; artificial vessels (e.g., artificial blood vessels, such as artificial arteries; and the like. A subject implantable ES-HyA material can comprise one or more active agents (as described below). A subject implantable ES-HyA material can be coated onto a solid substrate comprising a second material, where suitable second materials include, but are not limited to, calcium phosphate; titanium; and the like. A subject implantable ES-HyA material can be a tissue engineering scaffold. A subject implantable ES-HyA material can include living cells, e.g., stem cells; bone cells; bone progenitors; epithelial cells; neural cells; neural progenitor cells; endothelial cells; muscle cells; skin cells; and the like.

The present disclosure provides methods of treatment, comprising implanting into an individual in need thereof a subject implantable ES-HyA material. The present disclosure provides a method of treating a subject having a pathology characterized by diseased, damaged or loss of tissue, the method comprising implanting subject implantable ES-HyA material at or near the diseased, damaged or loss tissue of the subject, thereby inducing the formation of the tissue and treating the subject.

Where a subject implantable ES-HyA material comprises living cells, a subject method provides for tissue regeneration. Where a subject implantable ES-HyA material comprises an active agent such as a bone morphogenetic protein, a subject method provides for bone growth/bone regeneration. Where a subject implantable ES-HyA material comprises an active agent such as a clotting factor, a subject method provides for wound healing. Where a subject implantable ES-HyA material comprises an active agent such as an antibiotic, a subject method provides for wound healing.

The present disclosure provides a method of inducing ex vivo formation of a tissue, the method comprising: seeding a subject implantable ES-HyA matrix with cells in a medium suitable for proliferation, differentiation and/or migration of said cells, thereby inducing the formation of the tissue. The present disclosure provides a method of inducing in vivo formation of a tissue, the method comprising implanting a subject implantable ES-HyA material in a subject, where the implantable ES-HyA material comprises a subject ES-HyA matrix and living cells within the ES-HyA matrix, wherein said implanting induces the formation of the tissue.

Drug Delivery

A subject ES-HyA can be used as a drug delivery matrix; e.g., a subject ES-HyA can form a matrix. For example, an active agent is encapsulated within a subject ES-HyA matrix. An active agent can be embedded within a subject ES-HyA matrix. An active agent can be non-covalently associated with a subject ES-HyA matrix. An active agent can be covalently linked to a subject ES-HyA matrix.

Thus, the present disclosure provides an ES-HyA drug delivery composition comprising: a) a subject ES-HyA matrix; and b) an active agent associated with, embedded with, or encapsulated within, the ES-HyA matrix.

The present disclosure provides treatment methods comprising administering to an individual in need thereof a subject ES-HyA drug delivery composition, wherein the active agent is present in the ES-HyA drug delivery composition in an amount effective to treat a disease or disorder in the individual.

Active Agents

Active agents that can be included in a subject ES-HyA matrix include, but are not limited to, small molecule drugs, peptides, microRNAs (miRNA), and interfering RNAs. Small molecule drugs include drugs having a molecular weight of from about 5 Daltons to about 50 kDaltons (kDa) (e.g., from about 5 Daltons to about 10 Daltons, from about 10 Daltons to about 50 Daltons, from about 50 Daltons to about 100 Daltons, from about 100 Daltons to about 500 Daltons, from about 500 Daltons to about 1 kDa, from about 1 kDa to about 5 kDa, from about 5 kDa to about 10 kDa, from about 10 kDa to about 25 kDa, or from about 25 kDa to about 50 kDa), or from about 5 Daltons to about 5 kDa (e.g., from about 5 Daltons to about 10 Daltons, from about 10 Daltons to about 50 Daltons, from about 50 Daltons to about 100 Daltons, from about 100 Daltons to about 500 Daltons, from about 500 Daltons to about 1 kDa, or from about 1 kDa to about 5 kDa).

Pharmacologically active agents useful for inclusion in a subject ES-HyA matrix include drugs acting at synaptic and neuroeffector junctional sites (cholinergic agonists, anticholinesterase agents, atropine, scopolamine, and related antimuscarinic drugs, catecholamines and sympathomimetic drugs, and adrenergic receptor antagonists); drugs acting on the central nervous systems; autacoids (drug therapy of inflammation); drugs affecting renal function and electrolyte metabolism; cardiovascular drugs; drugs affecting gastrointestinal function; chemotherapy of neoplastic diseases; drugs acting on the blood and the blood-forming organs; and hormones and hormone antagonists. Thus, the agents useful in the matrix composition include, but are not limited to anti-infectives such as antibiotics and antiviral agents; analgesics and analgesic combinations; local and general anesthetics; anorexics; antiarthritics; antiasthmtic agents; anticonvulsants; antidepressants; antihistamines; anti-inflammatory agents; antinauseants; antimigrane agents; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorptioninhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including double- and single-stranded molecules and supercoiled or condensed molecules, gene constructs, expression vectors, plasmids, antisense molecules and the like.

Small Molecule Drugs

Any of a variety of small molecule active agents ("drugs") can be included in a subject ES-HyA matrix. Non-limiting examples include lipid-regulating agents; sex hormones; androgenic agents; antihypertensive agents; anti-diabetic agents; anti-viral agents; and active agents of any of the other below-listed categories.

Lipid-regulating agents that are generally classified as hydrophobic include HMG CoA reductase inhibitors such as atorvastatin, simvastatin, fluvastatin, pravastatin, lovastatin, cerivastatin, rosuvastatin, and pitavastatin, as well as other lipid-lowering ("antihyperlipidemic") agents such as bezafibrate, beclobrate, binifibrate, ciprofibrate, clinofibrate, clofibrate, clofibric acid, ezetimibe, etofibrate, fenofibrate, fenofibric acid, gemfibrozil, nicofibrate, pirifibrate, probucol, ronifibrate, simfibrate, and theofibrate.

Sex hormones include, e.g., progestins (progestogens), estrogens, and combinations thereof. Progestins include acetoxypregnenolone, allylestrenol, anagestone acetate, chlormadinone acetate, cyproterone, cyproterone acetate, desogestrel, dihydrogesterone, dimethisterone, ethisterone (17α-ethinyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, progesterone, and trimgestone. Also included within this general class are estrogens, e.g.: estradiol (i.e., 1,3,5-estratriene-3,17β-diol, or "17β-estradiol") and its esters, including estradiol benzoate, valerate, cypionate, heptanoate, decanoate, acetate and diacetate; 2-Methoxyestradiol; 4-Hydroxyestradiol; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. In many contexts, e.g., in female contraception and in hormone replacement therapy (HRT), a combination of a progestin and estrogen is used, e.g., progesterone and 17β-estradiol. For HRT, an androgenic agent may be advantageously included as well. Androgenic agents for this purpose include, for example, dehydroepiandrosterone (DHEA; also termed "prasterone"), sodium dehydroepiandrosterone sulfate, 4-dihydrotestosterone (DHT; also termed "stanolone"), and testosterone, and pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters.

Other androgenic agents include, but are not limited to, androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, ethylestrenol, oxandrolone, nandrolone phenpropionate, nandrolone decanoate, nandrolone furylpropionate, nandrolone cyclohexane-propionate, nandrolone benzoate, nandrolone cyclohexanecarboxylate, stanozolol, dromostanolone, and dromostanolone propionate.

Antihypertensive agents include, without limitation, amlodipine, benazepril, benidipine, candesartan, captopril, carvedilol, darodipine, dilitazem, diazoxide, doxazosin, enalapril, epleronone, eposartan, felodipine, fenoldopam, fosinopril, guanabenz, iloprost, irbesartan, isradipine, lercardinipine, lisinopril, losartan, minoxidil, nebivolol, nicardipine, nifedipine, nimodipine, nisoldipine, omapatrilat, phenoxybenzamine, prazosin, quinapril, reserpine, semotiadil, sitaxsentan, terazosin, telmisartan, and valsartan.

Anti-diabetic agents include, by way of example, acetohexamide, chlorpropamide, ciglitazone, farglitazar, glibenclamide, gliclazide, glipizide, glucagon, glyburide, glymepiride, miglitol, pioglitazone, nateglinide, pimagedine, repaglinide, rosiglitazone, tolazamide, tolbutamide, triampterine, and troglitazone.

Antiviral agents that can be included in a subject ES-HyA matrix include the antiherpes agents acyclovir, famciclovir, foscarnet, ganciclovir, idoxuridine, sorivudine, trifluridine, valacyclovir, and vidarabine, and other antiviral agents such as abacavir, amantadine, amprenavir, delviridine, didanosine, efavirenz, indinavir, interferon alpha, lamivudine, nelfinavir, nevirapine, ribavirin, rimantadine, ritonavir, saquinavir, stavudine, tipranavir, valganciclovir, zalcitabine, and zidovudine; and other antiviral agents such as abacavir, indinavir, interferon alpha, nelfinavir, ribavirin, rimantadine, tipranavir, ursodeoxycholic acid, and valganciclovir.

Additional suitable active agents include:

anti-inflammatory agents and non-opioid analgesics, such as aloxiprin, auranofin, azapropazone, azathioprine, benorylate, butorphenol, capsaicin, celecoxib, diclofenac, diflunisal, esonarimod, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, novantrone, oxaprozin, oxyphenbutazone, parecoxib, phenylbutazone, piclamilast, piroxicam, rofecoxib, ropivacaine, sulindac, tetrahydrocannabinol, tramadol, tromethamine, valdecoxib, and ziconotide, as well as the urinary analgesics phenazopyridine and tolterodine;

anti-angina agents, such as mibefradil, refludan, nahnefene, carvedilol, cromafiban, lamifiban, fasudil, ranolazine, tedisamil, nisoldipine, and tizanidine;

antihelminthics, such as albendazole, bephenium hydroxynaphthoate, cambendazole, dichlorophen, ivermectin, mebendazole, oxamniquine, oxfendazole, oxantel embonate, praziquantel, pyrantel embonate and thiabendazole;

anti-arrhythmic agents, such as amiodarone, disopyramide, flecainide acetate and quinidine sulfate;

anti-asthma agents, such as zileuton, zafirlukast, terbutaline sulfate, montelukast, and albuterol;

anti-bacterial agents, such as alatrofloxacin, azithromycin, baclofen, benethamine penicillin, cinoxacin, ciprofloxacin, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin, nalidixic acid, nitrofurantoin, norfloxacin, ofloxacin, rifampicin, rifabutine, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin;

anti-cancer agents and immunosuppressants, such as alitretinoin, aminoglutethimide, amsacrine, anastrozole, azathioprine, bexarotene, bicalutamide, biricodar, bisantrene, busulfan, camptothecin, candoxatril, capecitabine, cytarabine, chlorambucil, cyclosporin, dacarbazine, decitabine, ellipticine, estramustine, etoposide, gemcitabine, irinotecan, lasofoxifene, letrozole, lomustine, melphalan, mercaptopurine, methotrexate, mitomycin, mitotane, mitoxantrone, mofetil, mycophenolate, nebivolol, nilutamide, paclitaxel, palonosetron, procarbazine, ramipril, rubitecan, sirolimus, tacrolimus, tamoxifen, teniposide, testolactone, thalidomide, tirapazamine, topotecan, toremifene citrate, vitamin A, vitamin A derivatives, and zacopride;

anti-coagulants and other agents for preventing and treating stroke, such as cilostazol, citicoline, clopidogrel, cromafiban, dexanabinol, dicumarol, dipyridamole, nicoumalone, oprelvekin, perindopril erbumine, phenindione, ramipril, repinotan, ticlopidine, tirofiban, and heparin, including heparin salts formed with organic or inorganic bases, and low molecular weight heparin, i.e., heparin fragments generally having a weight average molecular weight in the range of about 1000 to about 10,000 D and exemplified by enoxaparin, dalteparin, danaproid, gammaparin, nadroparin, ardeparin, tinzaparin, certoparin, and reviparin;

anti-diabetics, such as acetohexamide, chlorpropamide, farglitazar, glibenclamide, gliclazide, glipizide, glimepiride, miglitol, nateglinide, pimagedine, pioglitazone, repaglinide, rosiglitazone, tolazamide, tolbutamide, troglitazone, and voglibose;

anti-epileptics, such as beclamide, carbamazepine, clonazepam, ethotoin, felbamate, fosphenytoin, lamotrigine, methoin, methsuximide, methylphenobarbitone, oxcarbazepine, paramethadione, phenacemide, phenobarbitone, phenytoin, phensuximide, primidone, sulthiame, tiagabine, topiramate, valproic acid, and vigabatrin;

anti-fungal agents, such as amphotericin, butenafine, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine, terconazole, tioconazole and undecenoic acid;

anti-gout agents, such as allopurinol, probenecid and sulphin-pyrazone;

antihistamines and allergy medications, such as acrivastine, astemizole, chlorpheniramine, cinnarizine, cetirizine, clemastine, cyclizine, cyproheptadine, desloratadine, dexchlorpheniramine, dimenhydrinate, diphenhydramine, epinastine, fexofenadine, flunarizine, loratadine, meclizine, mizolastine, oxatomide, and terfenadine;

anti-malarials, such as amodiaquine, chloroquine, chlorproguanil, halofantrine, mefloquine, proguanil, pyrimethamine and quinine sulfate;

agents for treating headaches, including anti-migraine agents, such as almotriptan, butorphanol, dihydroergotamine, dihydroergotamine mesylate, eletriptan, ergotamine, frovatriptan, methysergide, naratriptan, pizotyline, rizatriptan, sumatriptan, tonaberstat, and zolmitriptan;

anti-muscarinic agents, such as atropine, benzhexol, biperiden, ethopropazine, hyoscyamine, mepenzolate bromide, oxyphencyclimine, scopolamine, and tropicamide;

anti-protozoal agents, such as atovaquone, benznidazole, clioquinol, decoquinate, diiodohydroxyquinoline, diloxanide furoate, dinitolmide, furazolidone, metronidazole, nimorazole, nitrofirazone, ornidazole and tinidazole;

anti-thyroid agents, such as carbimazole, paricalcitol, and propylthiouracil;

anti-tussives, such as benzonatate;

anxiolytics, sedatives, and hypnotics, such as alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, dexmethylphenidate (d-threo-methylphenidate) diazepam, droperidol, ethinamate, flunanisone, flunitrazepam, triflupromazine, flupenthixol decanoate, fluphenazine, flurazepam, gabapentin, gaboxadol, γ-hydroxybutyrate, haloperidol, lamotrigine, lorazepam, lormetazepam, medazepam, meprobamate, mesoridazine, methaqualone, methylphenidate, midazolam, modafinil, molindone, nitrazepam, olanzapine, oxazepam, pentobarbitone, perphenazine pimozide, pregabalin, prochlorperazine, pseudoephedrine, quetiapine, rispiridone, sertindole, siramesine, sulpiride, sunepitron, temazepam, thioridazine, triazolam, zaleplon, zolpidem, and zopiclone;

appetite suppressants, anti-obesity drugs and drugs for treatment of eating disorders, such as amphetamine, bromocriptine, dextroamphetamine, diethylpropion, lintitript, mazindol, methamphetamine, orlistat, phentermine, and topiramate;

cardiovascular drugs, including: angiotensin converting enzyme (ACE) inhibitors such as enalapril, ramipril, perindopril erbumine, 1-carboxymethyl-3-1-carboxy-3-phenyl-(1S)-propylamino-2,3,4,5-tetrahydro-1H-(3S)-1-benzazepine-2-one, 3-(5-amino-1-carboxy-1S-pentyl)amino-2,3,4,5-tetrahydro-2-oxo-3S-1H-1-benzazepine-lacetic acid or 3-(1-ethoxycarbonyl-3-phenyl-(1S)-propylamino)-2,3,4,5-tetrahydro-2-oxo-(−3S)-benzazepi acid monohydrochloride; cardiac glycosides and cardiac inotropes such as amrinone, digoxin, digitoxin, enoximone, lanatoside C, medigoxin, and milrinone; calcium channel blockers such as verapamil, nifedipine, nicardipene, felodipine, isradipine, nimodipine, amlodipine and diltiazem; beta-blockers such as acebutolol, alprenolol, atenolol, labetalol, metoprolol, nadolol, oxyprenolol, pindolol, propafenone, propranolol, esmolol, sotalol, timolol, and acebutolol; antiarrhythmics such as moricizine, dofetilide, ibutilide, nesiritide, procainamide, quinidine, disopyramide, lidocaine, phenytoin, tocainide, mexiletine, flecainide, encainide, bretylium and amiodarone; cardioprotective agents such as dexrazoxane and leucovorin; vasodilators such as nitroglycerin; diuretic agents such as azetazolamide, amiloride, bendroflumethiazide, bumetanide, chlorothiazide, chlorthalidone, ethacrynic acid, furosemide, hydrochlorothiazide, metolazone, nesiritide, spironolactone, and triamterine; and miscellaneous cardiovascular drugs such as monteplase and corlopam;

corticosteroids, such as beclomethasone, betamethasone, budesonide, cortisone, desoxymethasone, dexamethasone, fludrocortisone, flunisolide, fluocortolone, fluticasone propionate, hydrocortisone, methylprednisolone, prednisolone, prednisone and triamcinolone;

erectile dysfunction drugs, such as apomorphine, phentolamine, and vardenafil;

gastrointestinal agents, such as alosetron, bisacodyl, cilansetron, cimetidine, cisapride, diphenoxylate, domperidone, esomeprazole, famotidine, granisetron, lansoprazole, loperamide, mesalazine, nizatidine, omeprazole, ondansetron, prantoprazole, rabeprazole sodium, ranitidine, risperidone, sulphasalazine, and tegaserod;

keratolytics, such as such as acetretin, calcipotriene, calcifediol, calcitriol, cholecalciferol, ergocalciferol, etretinate, retinoids, targretin, and tazarotene;

lipid regulating agents, such as atorvastatin, bezafibrate, cerivastatin, ciprofibrate, clofibrate, ezetimibe, fenofibrate, fluvastatin, gemfibrozil, pitavastatin, pravastatin, probucol, rosuvastatin, and simvastatin;

muscle relaxants, such as cyclobenzaprine, dantrolene sodium and tizanidine HCl;

agents to treat neurodegenerative diseases, including active agents for treating Alzheimer's disease such as akatinol, donezepil, donepezil hydrochloride, dronabinol, galantamine, neotrofin, rasagiline, physostigmine, physostigmine salicylate, propentoffyline, quetiapine, rivastigmine, tacrine, tacrine hydrochloride, thalidomide, and xaliproden; active agents for treating Huntington's Disease, such as fluoxetine and carbamazepine; anti-parkinsonism drugs useful herein include amantadine, apomorphine, bromocriptine, entacapone, levodopa (particularly a levodopa/carbidopa combination), lysuride, pergolide, pramipexole, rasagiline, riluzole, ropinirole, selegiline, sumanirole, tolcapone, trihexyphenidyl, and trihexyphenidyl hydrochloride; and active agents for treating ALS such as the anti-spastic agents baclofen, diazemine, and tizanidine;

nitrates and other anti-anginal agents, such as amyl nitrate, glyceryl trinitrate, isosorbide dinitrate, isosorbide mononitrate and pentaerythritol tetranitrate;

neuroleptic drugs, including antidepressant drugs, antimanic drugs, and antipsychotic agents, wherein antidepressant drugs include (a) the tricyclic antidepressants such as amoxapine, amitriptyline, clomipramine, desipramine, doxepin, imipramine, maprotiline, nortriptyline, protriptyline, and trimipramine, (b) the serotonin reuptake inhibitors citalopram, fluoxetine, fluvoxamine, paroxetine, sertraline, and venlafaxine, (c) monoamine oxidase inhibitors such as phenelzine, tranylcypromine, and (−)-selegiline, and (d) other antidepressants such as aprepitant, bupropion, duloxetine, gepirone, igmesine, lamotrigine, maprotiline, mianserin, mirtazapine, nefazodone, rabalzotan, sunepitron, trazodone and venlafaxine, and wherein antimanic and antipsychotic agents include (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride, (b) thioxanthenes such as chlorprothixene, thiothixene, and thiothixene hydrochloride, and (c) other heterocyclic drugs such as carbamazepine, clozapine, droperidol, haloperidol, haloperidol decanoate, loxapine succinate, molindone, molindone hydrochloride, olanzapine, pimozide, quetiapine, risperidone, and sertindole;

nutritional agents, such as calcitriol, carotenes, dihydrotachysterol, essential fatty acids, non-essential fatty acids, phytonadiol, vitamin A, vitamin $B_2$, vitamin D, vitamin E and vitamin K;

opioid analgesics, such as alfentanil, apomorphine, buprenorphine, butorphanol, codeine, dextropropoxyphene, diamorphine, dihydrocodeine, fentanyl, hydrocodone, hydromorphone, levorphanol, meperidine, meptazinol, methadone, morphine, nalbuphine, oxycodone, oxymorphone, pentazocine, propoxyphene, sufentanil, and tramadol; and stimulants, including active agents for treating narcolepsy, attention deficit disorder (ADD) and attention deficit hyperactivity disorder (ADHD), such as amphetamine, dexamphetamine, dexfenfluramine, fenfluramine, mazindol, methylphenidate (including d-threo-methylphenidate, or "dexmethylphenidate," as well as racemic d,l-threo-methylphenidate), modafinil, pemoline, and sibutramine.

Hydrophobic Active Agents

Non-limiting examples of hydrophobic active agents include, but are not limited to, acetretin, acetyl coenzyme Q, albendazole, albuterol, aminoglutethimide, amiodarone, amlodipine, amphetamine, amphotericin B, atorvastatin, atovaquone, azithromycin, baclofen, beclomethasone, benazepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicumarol, digoxin, dehydroepiandrosterone, dihydroergotamine, dihydrotachysterol, dirithromycin, donezepil, efavirenz, eposartan, ergocalciferol, ergotamine, essential fatty acid sources, estradiol, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thyroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nisoldipine, nilutanide, nitro furantoin, nizatidine, omeprazole, oprevelkin, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, repaglinide, rifabutine, rifapentine, rimexolone, ritanovir, rizatriptan, rofecoxib, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofiban, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, zopiclone, and combinations thereof.

Hydrophilic Active Agents

Non-limiting examples of hydrophilic active agents include, without limitation, acarbose, acyclovir, acetyl cysteine, acetylcholine chloride, alatrofloxacin, alendronate, alglucerase, amantadine hydrochloride, ambenomium, amifostine, amiloride hydrochloride, aminocaproic acid, amphotericin B, antihemophilic factor (human), antihemophilic factor (porcine), antihemophilic factor (recombinant), aprotinin, asparaginase, atenolol, atracurium besylate, atropine, azithromycin, aztreonam, BCG vaccine, bacitracin, becaplermin, belladona, bepridil hydrochloride, bleomycin sulfate, calcitonin human, calcitonin salmon, carboplatin, capecitabine, capreomycin sulfate, cefamandole nafate, cefazolin sodium, cefepime hydrochloride, cefixime, cefonicid sodium, cefoperazone, cefotetan disodium, cefotaxime, cefoxitin sodium, ceftizoxime, ceftriaxone, cefuroxime axetil, cephalexin, cephapirin sodium, cholera vaccine, chorionic gonadotropin, cidofovir, cisplatin, cladribine, clidinium bromide, clindamycin and clindamycin derivatives, ciprofloxacin, clodronate, colistimethate sodium, colistin sulfate, corticotropin, cosyntropin, cromolyn sodium, cytarabine, dalteparin sodium, danaparoid, deferoxamine, denileukin diftitox, desmopressin, diatrizoate meglumine and diatrizoate sodium, dicyclomine, didanosine, dirithromycin, dopamine hydrochloride, dornase alpha, doxacurium chloride, doxorubicin, etidronate disodium, enalaprilat, enkephalin, enoxaparin, enoxaprin sodium, ephedrine, epinephrine, epoetin alpha, erythromycin, esmolol hydrochloride, factor IX, famciclovir, fludarabine, fluoxetine, foscamet sodium, ganciclovir, granulocyte colony stimulating factor, granulocyte-macrophage stimulating factor, recombinant human growth hormone, bovine growth hormine, gentamycin, glucagon, glycopyrolate, gonadotropin releasing hormone and synthetic analogs thereof, gonadorelin, grepafloxacin, haemophilus B conjugate vaccine, hepatitis A virus vaccine inactivated, hepatitis B virus vaccine inactivated, heparin sodium, indinavir sulfate, influenza virus vaccine, interleukin-2, interleukin-3, insulin-human, insulin lispro, insulin procine, insulin NPH, insulin aspart, insulin glargine, insulin detemir, interferon alpha, interferon beta, ipratropium bromide, ifosfamide, Japanese encephalitis virus vaccine, lamivudine, leucovorin calcium, leuprolide acetate, levofloxacin, lincomycin and lincomycin derivatives, lobucavir, lomefloxacin, loracarbef, mannitol, measles virus vaccine, meningococcal vaccine, menotropins, mepenzolate bromide, mesalamine, methenamine, methotrexate, methscopolamine, metformin hydrochloride, metoprolol, mezlocillin sodium, mivacurium chloride, mumps viral vaccine, nedocromil sodium, neostigmine bromide, neostigmine methyl sulfate, neurontin, norfloxacin, octreotide acetate, ofloxacin, olpadronate, oxytocin, pamidronate disodium, pancuronium bromide, paroxetine, perfloxacin, pentamidine isethionate, pentostatin, pentoxifylline, penciclovir, pentagastrin, phentolamine mesylate, phenylalanine, physostigmine salicylate, plague vaccine, piperacillin sodium, platelet derived growth factor, pneumococcal vaccine polyvalent, poliovirus vaccine (inactivated), poliovirus vaccine live (OPV), polymyxin B sulfate, pralidoxime chloride, pramlintide, pregabalin, propafenone, propenthaline bromide, pyridostigmine bromide, rabies vaccine, risedronate, ribavirin, rimantadine hydrochloride, rotavirus vaccine, salmeterol xinafoate, sincalide, small pox vaccine, solatol, somatostatin, sparfloxacin, spectinomycin, stavudine, streptokinase, streptozocin, suxamethonium chloride, tacrine hydrochloride, terbutaline sulfate, thiopeta, ticarcillin, tiludronate, timolol, tissue type plasminogen activator, TNFR:Fc, TNK-tPA, trandolapril, trimetrexate gluconate, trospectomycin, trovafloxacin, tubocurarine chloride, tumor necrosis factor, typhoid vaccine live, urea, urokinase, vancomycin, valacyclovir, valsartan, varicella virus vaccine live, vasopressin and vasopressin derivatives, vecuronium bromide, vinblastine, vincristine, vinorelbine, vitamin B12, warfarin sodium, yellow fever vaccine, zalcitabine, zanamivir, zolendronate, zidovudine, and combinations thereof.

Polypeptide Agents

Peptidyl drugs include therapeutic peptides and proteins per se, whether naturally occurring, chemically synthesized, recombinantly produced, and/or produced by biochemical (e.g., enzymatic) fragmentation of larger molecules, and may contain the native sequence or an active fragment thereof. Specific peptidyl drugs include, without limitation, the peptidyl hormones activin, amylin, angiotensin, atrial natriuretic peptide (ANP), calcitonin, calcitonin gene-related peptide, calcitonin N-terminal flanking peptide, ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, gonadotropin-releasing factor (GnRF or GNRH), growth hormone releasing factor (GRF, GRH), human chorionic gonadotropin (hCH), inhibin A, inhibin B, insulin, luteinizing hormone (LH), luteinizing hormone-releasing hormone (LHRH), α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, vasoactive intestinal peptide (VIP), and vasopressin. Other peptidyl drugs are the cytokines, e.g., colony stimulating factor 4, heparin binding neurotrophic factor (HBNF), interferon-α, interferon α-2a, interferon α-2b, interferon α-n3, interferon-β, etc., interleukin-1, interleukin-2, interleukin-3, interleukin-4, interleukin-5, interleukin-6, etc., tumor necrosis factor, tumor necrosis factor-α, granuloycte colony-stimulating factor (G-CSF), granulocyte-macrophage colony-stimulating factor (GM-CSF), macrophage colony-stimulating factor, midkine (MD), and thymopoietin. Still other peptidyl drugs that can be advantageously delivered using the methodology and formulations of the present invention include endorphins (e.g., dermorphin, dynorphin, α-endorphin, β-endorphin, γ-endorphin, sigma-endorphin, [Leu$^5$]enkephalin, [Met$^5$]enkephalin, substance P), kinins (e.g., bradykinin, potentiator B, bradykinin potentiator C, kallidin), LHRH analogues (e.g., buserelin, deslorelin, fertirelin, goserelin, histrelin, leuprolide, lutrelin, nafarelin, tryptorelin), and the coagulation factors, such as α$_1$-antitrypsin, α$_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor), plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, and thrombomodulin and combinations thereof RNAi Interfering RNA (RNAi) include, e.g., antisense RNA, a ribozyme, an RNAi and an siRNA. RNAi fragments, particularly double-stranded (ds) RNAi, can be used to inhibit gene expression. One approach well known in the art for inhibiting gene expression is short interfering RNA (siRNA) mediated gene silencing, where the level of expression product of a target gene is reduced by specific double stranded siRNA nucleotide sequences that are complementary to at least a 19-25 nucleotide long segment (e.g., a 20-21 nucleotide sequence) of the target gene transcript, including the 5' untranslated (UT) region, the ORF, or the 3' UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858; and U.S. Patent Publication No. 20040023390 for descriptions of siRNA technology. The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal.

Target genes include any gene encoding a target gene product (RNA or protein) that is deleterious (e.g., pathological); a target gene product that is malfunctioning; a target gene product. Target gene products include, but are not limited to, huntingtin; hepatitis C virus; human immunodeficiency virus; amyloid precursor protein; tau; a protein that includes a polyglutamine repeat; a herpes virus (e.g., varicella zoster); any pathological virus; and the like.

siRNA is useful for treating a variety of disorders and conditions, including, but not limited to, neurodegenerative diseases, e.g., a trinucleotide-repeat disease, such as a disease associated with polyglutamine repeats, e.g., Huntington's disease, spinocerebellar ataxia, spinal and bulbar muscular atrophy (SBMA), dentatorubropallidoluysian atrophy (DRPLA), etc.; an acquired pathology (e.g., a disease or syndrome manifested by an abnormal physiological, biochemical, cellular, structural, or molecular biological state) such as a viral infection, e.g., hepatitis that occurs or may occur as a result of an HCV infection, acquired immunodeficiency syndrome, which occurs as a result of an HIV infection; and the like.

In some embodiments, an siRNA is directed against a member of a signal transduction pathway, e.g., the insulin pathway, including AKT1-3, CBL, CBLB, EIF4EBP1, FOXO1A, FOXO3A, FRAP1, GSK3A, GSK3B, IGF1, IGF1R, INPP5D, INSR, IRS1, MLLT7, PDPK1, PIK3CA, PIK3CB, PIK3R1, PIK3R2, PPP2R2B, PTEN, RPS6, RPS6KA1, RPX6KA3, SGK, TSC1, TSC2, and XPO1); an apoptotic pathway (CASP3,6,7,8,9, DSH1/2, P110, P85, PDK1/2, CATENIN, HSP90, CDC37, P23, BAD, BCLXL, BCL2, SMAC, and others); and pathways involved in DNA damage, cell cycle, and the like (p53, MDM2, CHK1/2, BRCA1/2, ATM, ATR, P15INK4, P27, P21, SKP2, CDC25C/A, 14-3-3, PLK, RB, CDK4, GLUT4, Inos, Mtor, FKBP, PPAR, RXR, ER). Similarly, genes involved in immune system function including TNFR1, IL-IR, IRAK1/2, TRAF2, TRAF6, TRADD, FADD, IKKε, IKKγ, IKKβ, IKKα, IkBα, IkBβ, p50, p65, Rac, RhoA, Cdc42, ROCK, Pak1/2/3/4/5/6, cIAP, HDAC1/2, CBP, β-TrCP, Rip2/4, and others are also important targets for siRNAs, where such siRNAs can be useful in treating immune system disorders. siRNAs specific for gene products involved in apoptosis, such as Dsh1/2, PTEN, P110 (pan), P85, PDK1/2, Akt1, Akt2, Akt (pan), $p70^{S6K}$, GSK3β, PP2A (cat), β-catenin, HSP90, Cdc37/p50, P23, Bad, BclxL, Bc12, Smac/Diablo, and Ask1 are useful in the treatment of diseases that involve defects in programmed cell death (e.g. in the treatment of cancer). siRNA agents directed against p53, MDM2, Chk1/2, BRCA1/2, ATM, ATR, $p15^{INK4}$, P27, P21, Skp2, Cdc25C/A, 14-3-3sigma/ε, PLK, Rb, Cdk4, Glut4, iNOS, mTOR, FKBP, PPARγ, RXRα, ERα, and related genes can be used to treat diseases associated with disruptions in DNA repair, and cell cycle abnormalities, where such diseases include cancer. Examples of such siRNAs and targets are known in the art; see, e.g., US Patent Publication No. 2005/0246794. For example, a recombinant retroviral vector that includes a heterologous nucleic acid encoding an siRNA is useful for treating disorders resulting from or associated with dysregulated cell cycle, e.g., cancer.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Sulfonation of Hyaluronic Acid

ES-HyA was synthesized using via conjugation of the aminoethylsulfonate to the HyA backbone. The ability of ES-HyA to resist enzymatic degradation relative to HyA was evaluated by incubating ES-HyA and HyA with hyaluronidase at various concentrations for 2.5 hours (FIG. 1). The cumulative molecular weight distribution was evaluated at various time points during the experimental interval using size exclusion chromatography with multi-angle light scattering analysis (SEC-MALS). It was found that the ES-HyA was able to resist the activity of the glycolytic enzyme, exhibited by molecular weights that were 2-3 times greater than the HyA at physiologically relavant concentrations of hyaluronidase (0.25-2.5 units/mL). At these concentrations, the half-life of ES-HyA appeared to be in the range of 6.6-26.9 hrs, whereas the half-life of HyA was in the range of 2.35-7.5. Thus the method of sulfonation increased the half-life of the biopolymer by approximately 3× on a concentration controlled basis.

The sulfur content of the ES-HyA was evaluated to estimate the degree of sulfonation that was required to achieve this improved glycolytic resistance, and it was estimated that the substation ratio was approximately 10% (FIG. 2). This would indicate that for every 10 disaccharide HyA units, there was one conjugated ethylsulfonate. The other 90% of HyA units are unmodified and able to participate in conjugation reactions with other functionalized molecules. These results were verified by conjugating HyA and ES-HyA with EMCH, a heterobifunctional crosslinker that reacts with the carboxylic acid group on the HyA disaccharide, at various stoichiometric ratios (FIG. 3). It was found that the sulfonation of ES-HyA had little effect on the conjugation reaction, although there is evidence that the available binding sites per HyA molecule may saturate at lower conjugation ratios, which is likely due to the previous conjugation reaction with aminoethylsulfonate.

These results indicate that the method of sulfonation could dramatically improve the utility of HyA in medical technologies. Previous methods of stabilizing HyA using sulfation or sulfonation require high-substitution ratios (2-4 sulfates per HyA disaccharide unit) and the reactions must be performed in organic solvents. By contrast, the method described above can be carried out in aqueous solutions; thus the ES-HyA products can be more readily translated into biocompatible products. It has been demonstrated that the stability of ES-HyA is achieved with dramatically fewer sulfonate groups per HyA disaccharide unit. Thus, the ES-HyA can be further modified and used as a substrate for a variety of medical technologies.

Example 2: Synthesis of Sulfated Hyaluronic Acid

Sulfated hyaluronic acid was synthesized by a two-step process. First, aldehyde derivative of hyaluronic acid (HyAALD) was synthesized by sodium periodate oxidation of hyaluronic acid (HyA). HyA of 1 million Daltons was incubated with sodium periodate ($NaIO_4$) in the dark at room temperature to convert the vicinal diols to adjacent aldehydes to produce HyAALD (FIG. 4A). Second, sulfated hyaluronic acid (SHyA) was synthesized by conjugation of 2-aminoethyl hydrogen sulfate to HyAALD and subsequent reduction using sodium cynoborohydride. HyAALD produced in the first reaction step was combined with 2-aminoethyl hydrogen sulfate ($NHCH_2CH_2-SO_4^-$) and the reaction product was incubated with sodium cynoborohydride ($NaBH_3CN$) at room temperature to produce SHyA (FIG. 4B).

Figure 5A:
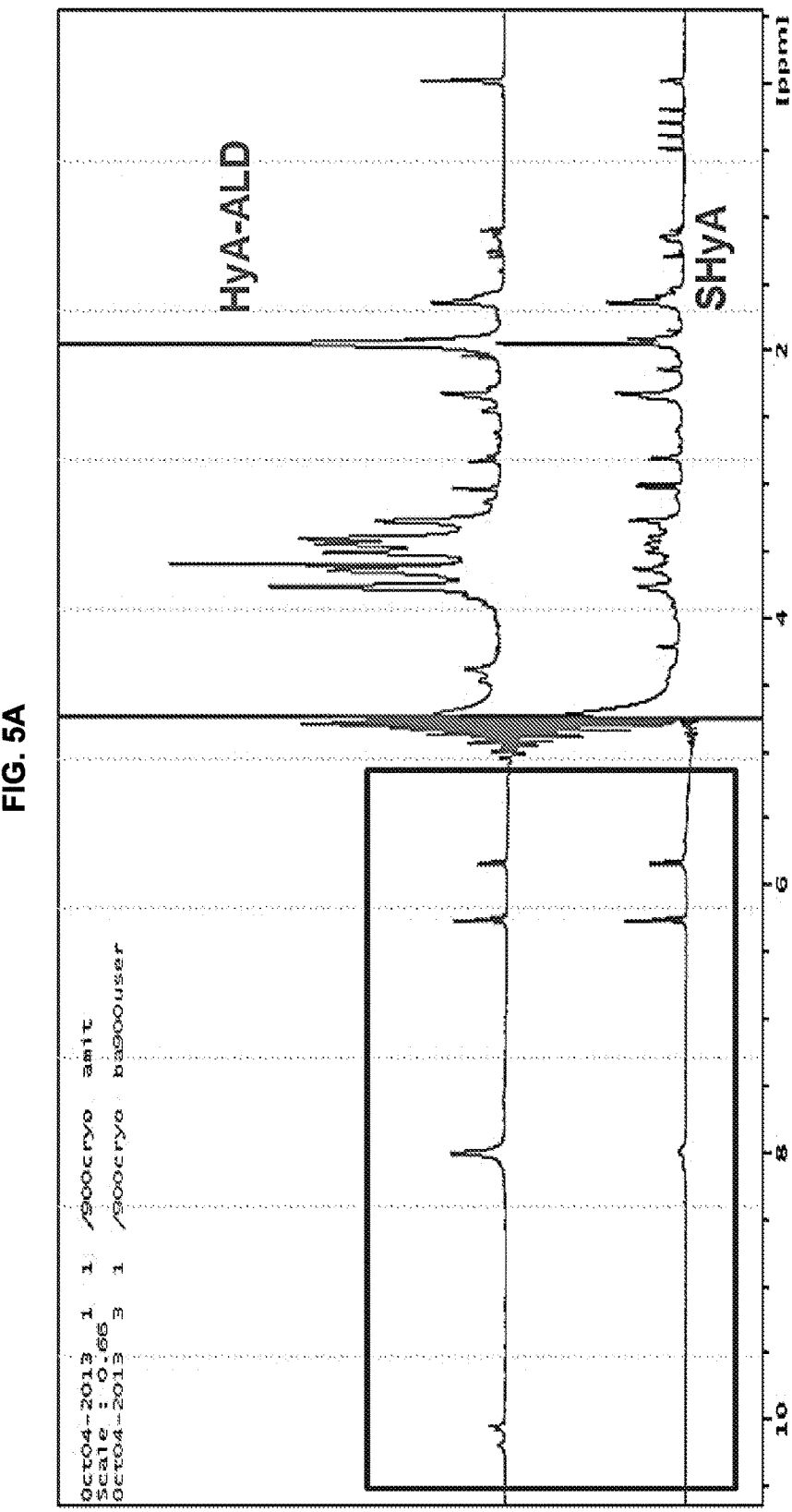
FIGS. 5A-B depict Proton ($^1$H) NMR validation of hyaluronic acid sulfation.
Figure 5B:
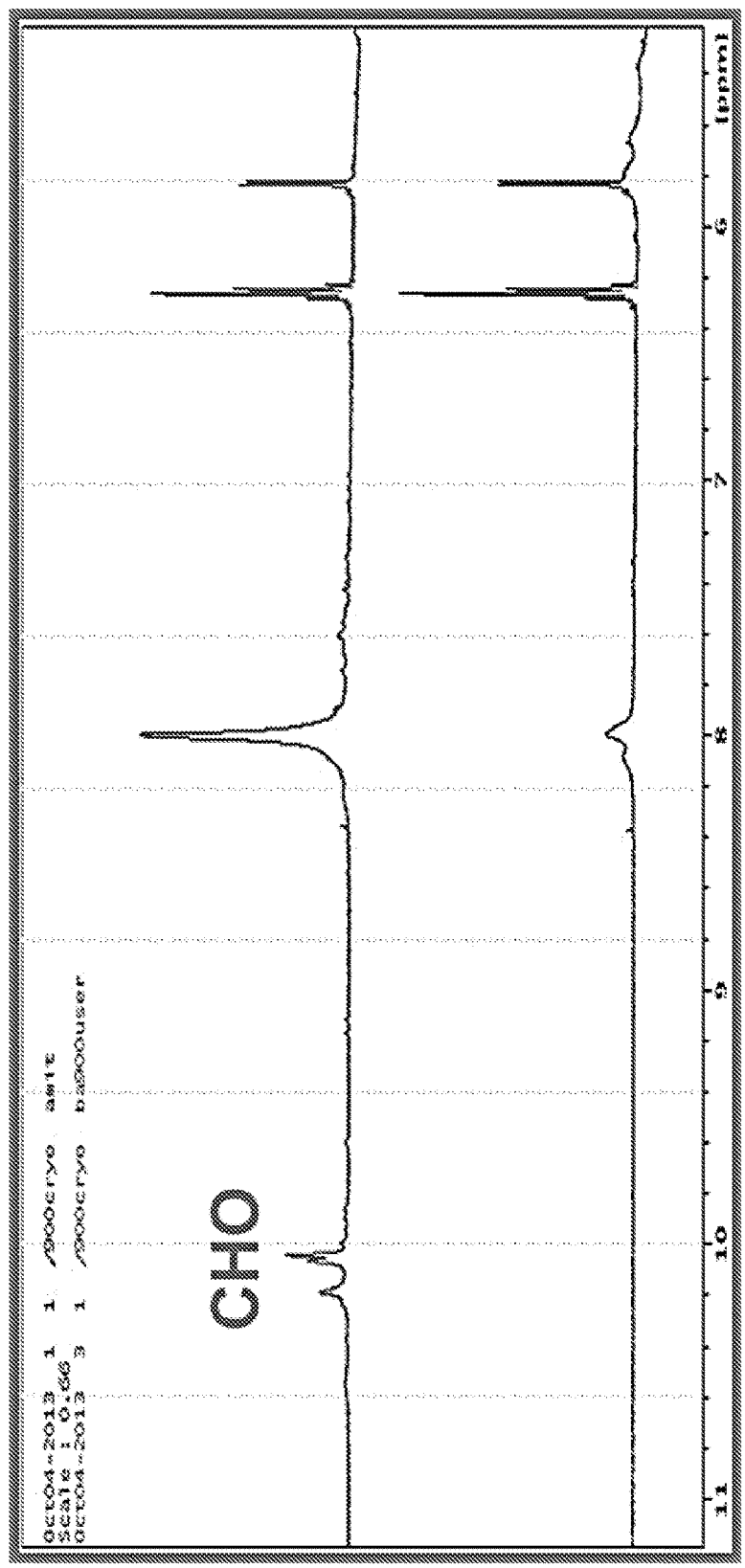

Validation of sulfation of hyaluronic acid was performed by NMR analysis. Proton-($^1H$)-NMR spectra were produced and compared for HyAALD and SHyA to demonstrate the disappearance of aldehyde groups following reaction of HyAALD with 2-aminoethyl hydrogen sulfate (FIG. 5A). FIG. 5B, a zoom-in of the area boxed in FIG. 5A, clearly indicated a lack of aldehyde peaks (CHO) in SHyA as compared to HyAADL.

Figure 6:
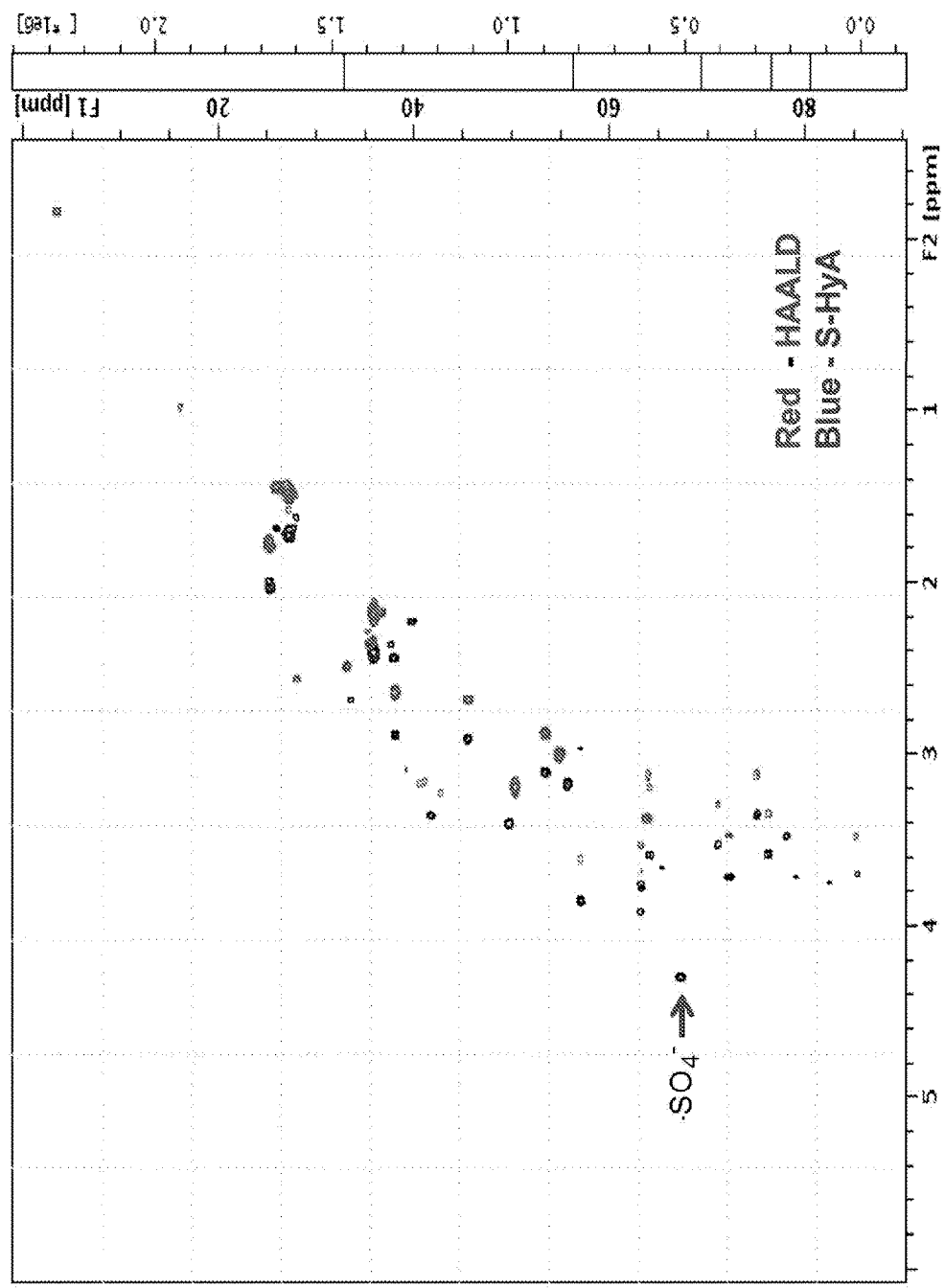
FIG. 6 depicts Proton ($^1$H)-Carbon ($^{13}$C) NMR validation of hyaluronic acid sulfation.

Further validation of sulfation of hyaluronic acid was performed by 2D Proton ($^1H$)-Carbon ($^{13}C$) NMR analysis. 2D Proton ($^1H$)-Carbon ($^{13}C$) NMR spectra were produced and compared for HyAALD and SHyA to demonstrate the presence of sulfate groups ($SO_4^-$) on sulfated hyaluronic acid (SHyA) (FIG. 6).

Figure 7:
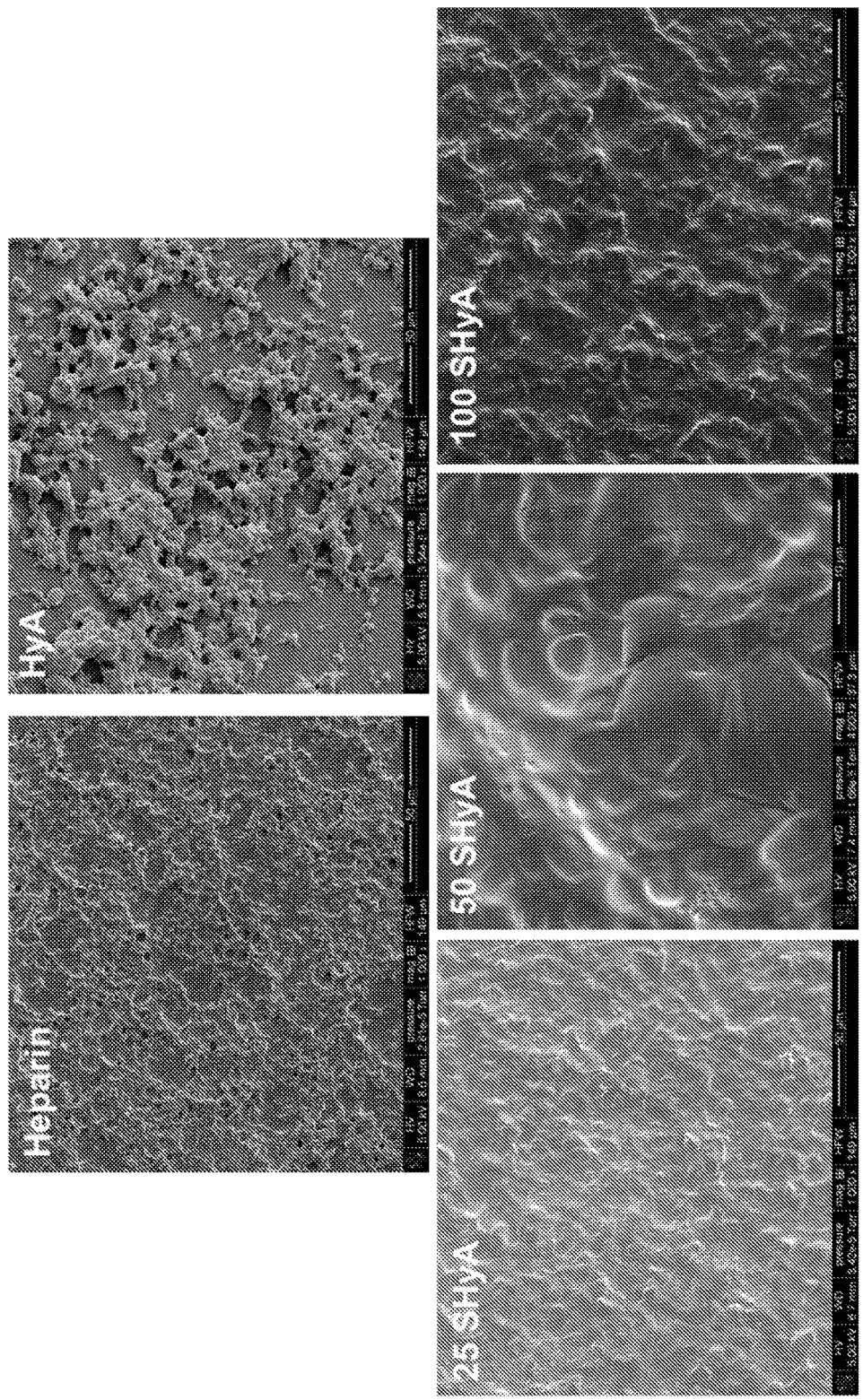
FIG. 7 depicts functional validation of hyaluronic acid sulfation by platelet adhesion assay.

Functional validation of sulfation of hyaluronic acid was performed by platelet adhesion assay. Platelet rich plasma (PRP) was collected from blood and used for platelet adhesion experiment performed on heparin, native hyaluronic acid (HyA), and sulfated hyaluronic acid (SHyA)

with varied degrees of sulfation. Degree of sulfation was varied by varying the moles of 2-aminoethyl hydrogen sulfate reacted with HyAALD (25, 50, or 100 moles of 2-aminoethyl hydrogen sulfate). Platelet adhesion experiments were visualized by scanning electron microscope (SEM) imaging (FIG. 7). The experiment demonstrated platelet aggregation on native HyA but no aggregation of platelets on SHyA or heparin control.

Figure 8:
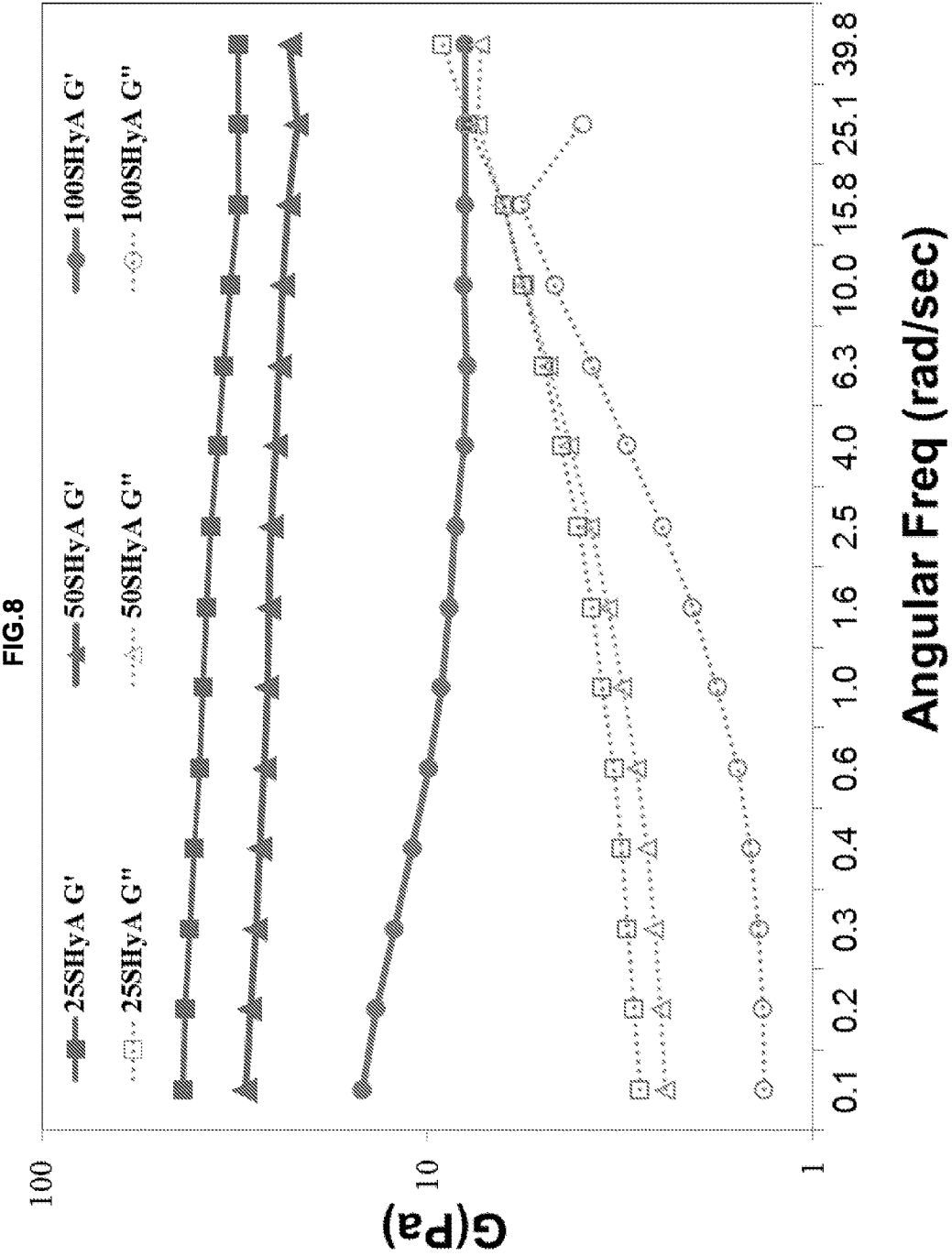
FIG. 8 depicts functional validation of hyaluronic acid sulfation by platelet poor plasma clotting assay.

Further functional validation of sulfation of hyaluronic acid was performed by clotting assay on platelet poor plasma. Platelet poor plasma (PPP) was collected from blood and recalcified in the presence of sulfated hyaluronic acid (SHyA) with varied degrees of sulfation. Degree of sulfation was varied by varying the moles of 2-aminoethyl hydrogen sulfate reacted with HyAALD (25, 50, or 100 moles of 2-aminoethyl hydrogen sulfate). The modulus of clot formed by recalcification of PPP was analyzed on oscillatory rheometer and the results were plotted (FIG. 8). The experiment demonstrated that the modulus of clotted PPP decreased with the increase of degree of sulfation as higher sulfation inhibits the recalcification of PPP.

Figure 9:
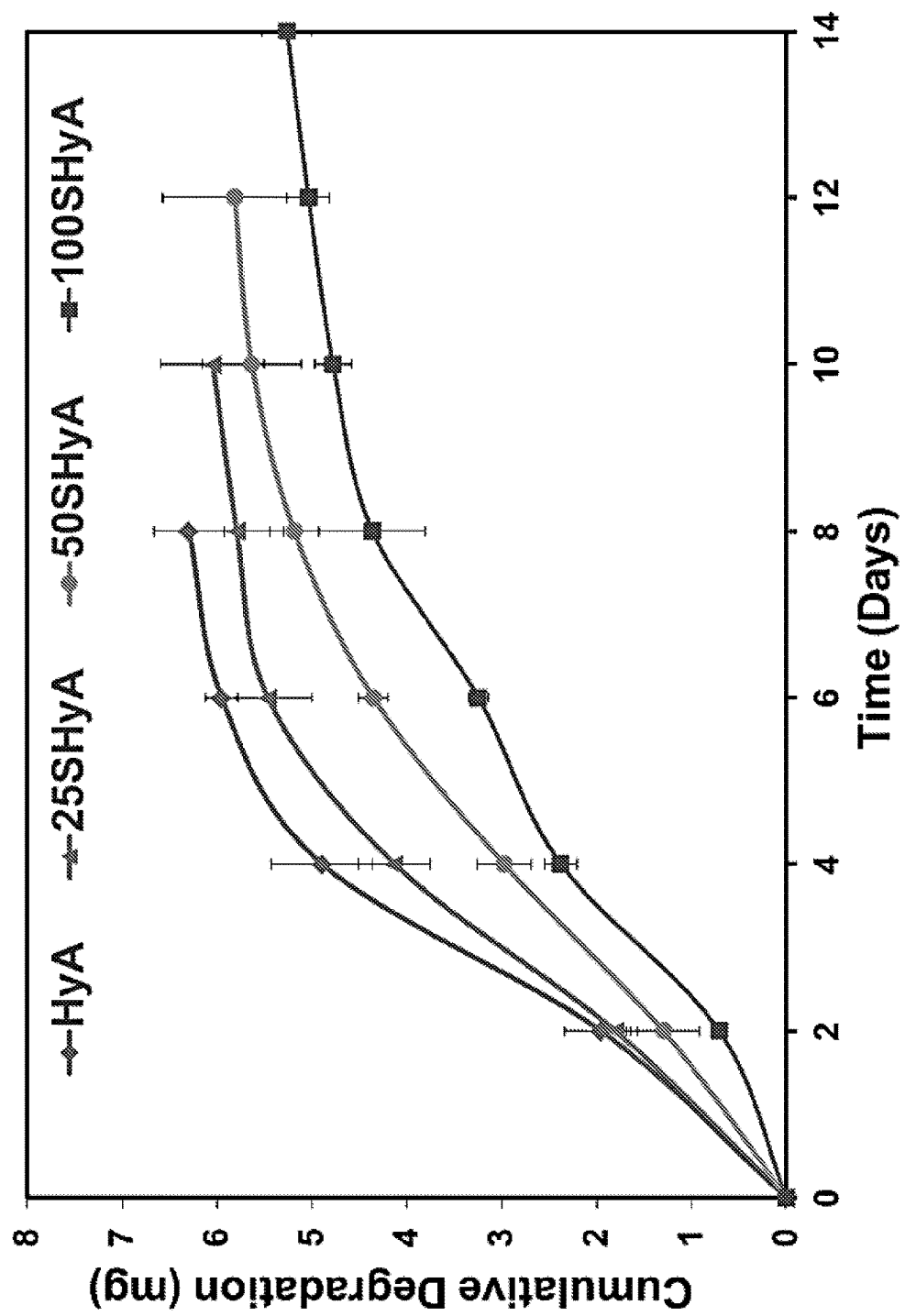
FIG. 9 depicts functional validation of hyaluronic acid sulfation by carbazole assay.

Further functional validation of sulfation of hyaluronic acid was performed by carbazole assay. Enzymatic degradation of HyA and sulfated hyaluronic acid (SHyA) with varied degrees of sulfation was measured by carbazole assay in 15 U/mL of HAase solution at pH 7.4. Degree of sulfation was varied by varying the moles of 2-aminoethyl hydrogen sulfate reacted with HyAALD (25, 50, or 100 moles of 2-aminoethyl hydrogen sulfate). Cumulative degradation was plotted over time (FIG. 9). The experiment demonstrated that the enzymatic stability of HyA increased with increasing degrees of sulfation.

Figure 10:
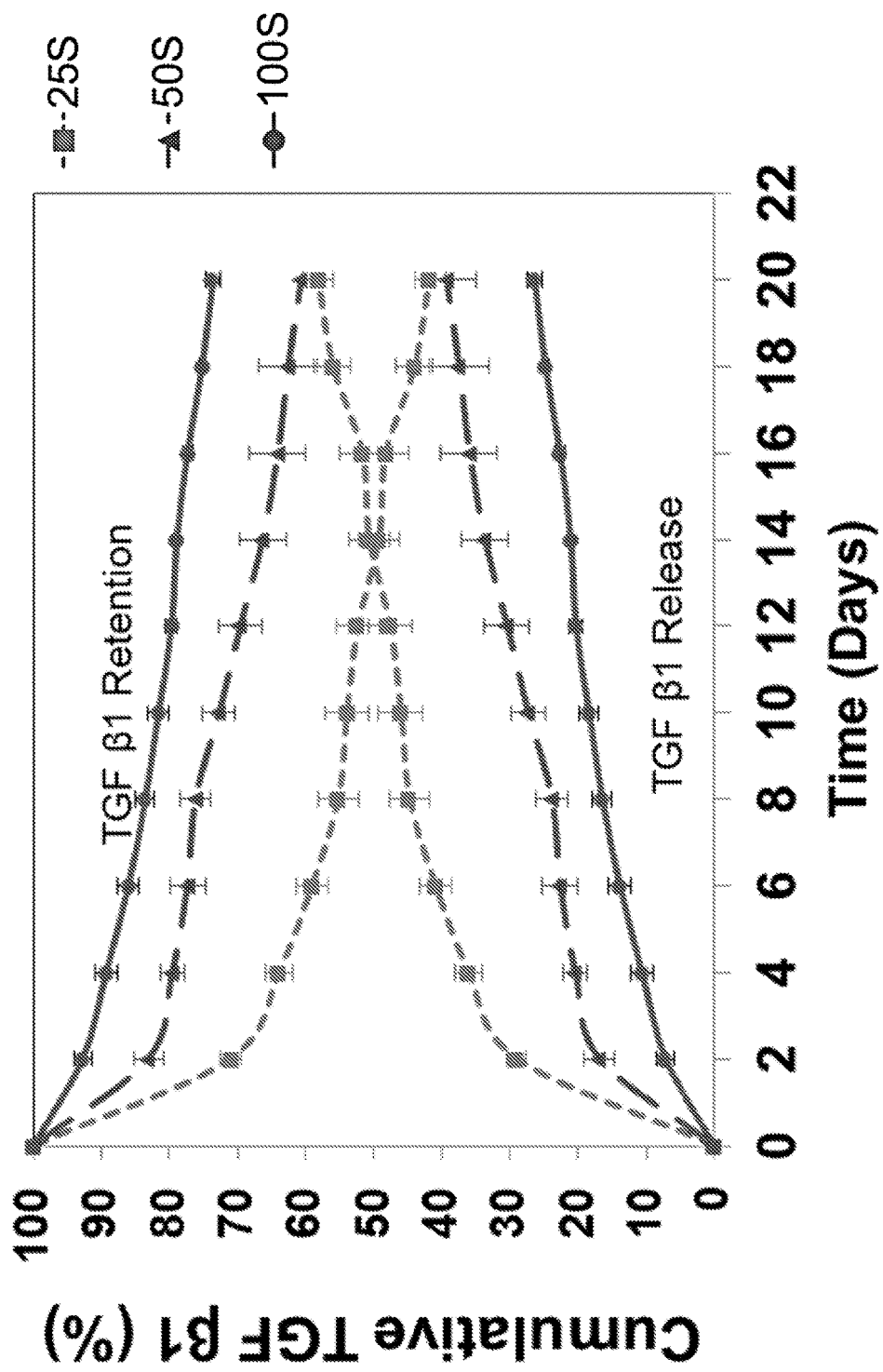
FIG. 10 depicts functional validation of hyaluronic acid sulfation by retention kinetics assay.

Further functional validation of sulfation of hyaluronic acid was performed by retention kinetics assay. The kinetics of retention of TGFβ1 was measured in sulfated hyaluronic acid (SHyA) with varied degrees of sulfation. Degree of sulfation was varied by varying the moles of 2-aminoethyl hydrogen sulfate reacted with HyAALD (25, 50, or 100 moles of 2-aminoethyl hydrogen sulfate). The percentage of 40 nM TGFβ1 retained by the differently sulfated hydrogels was determined by ELISA and plotted over time (FIG. 10). The experiment demonstrated that retention of TGFβ1 is dependent on the degree of sulfation of the SHyA with the most sulfated HyA hydrogels (100SHyA) retaining over 70% of the TGFβ1 for up to 20 days.

Example 3: Effects of HyA Sulfation on Cells

Figure 11:
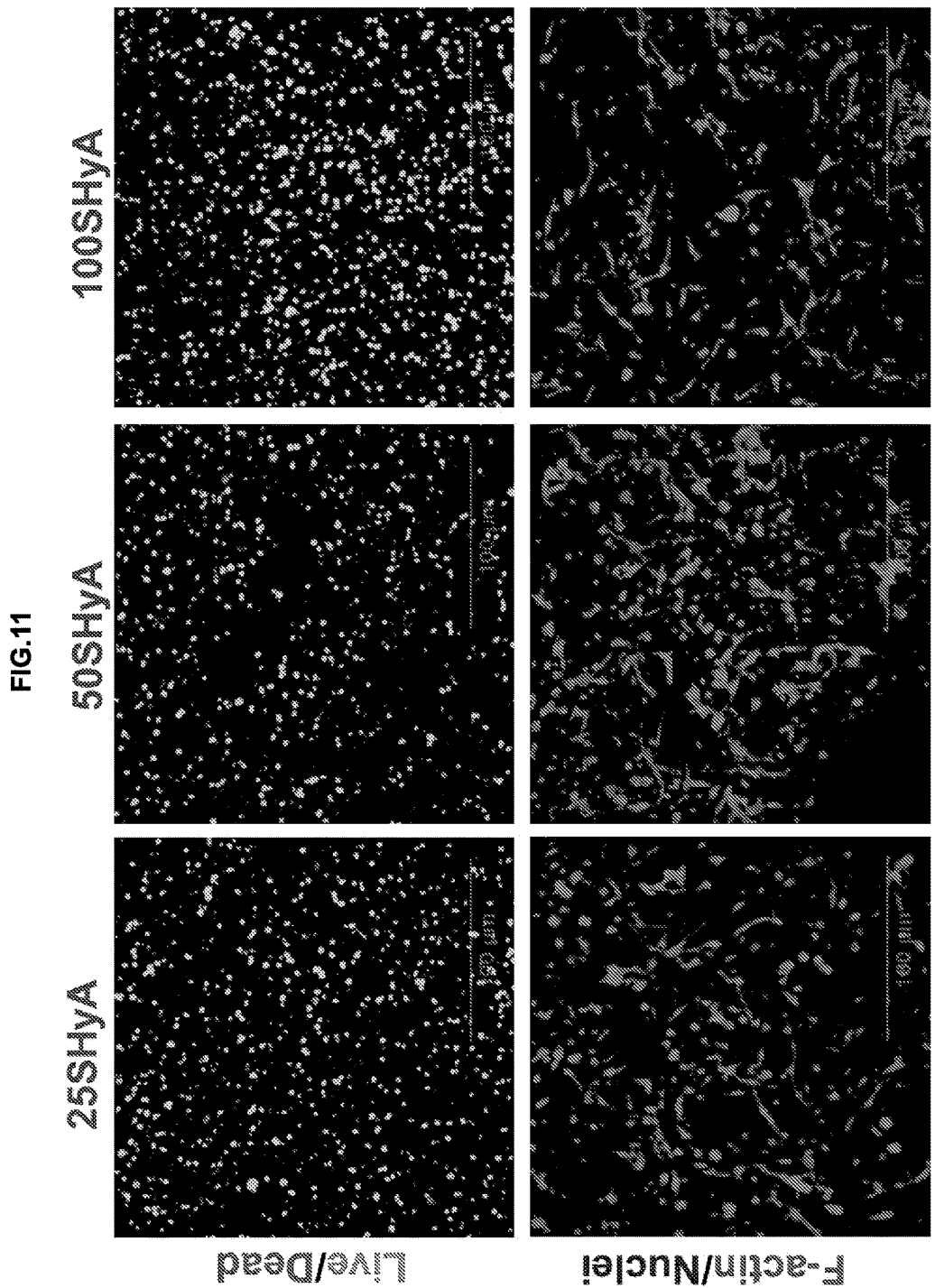
FIG. 11 depicts the effects of sulfation of hyaluronic acid on cell viability, proliferation and adhesion.

The viability, proliferation, and adhesion of cardiac progenitor cells (CPC) was assessed in sulfated hyaluronic acid (SHyA) with varied degrees of sulfation. Degree of sulfation was varied by varying the moles of 2-aminoethyl hydrogen sulfate reacted with HyAALD (25, 50, or 100 moles of 2-aminoethyl hydrogen sulfate). Cells encapsulated in sulfated HyA hydrogels demonstrated high viability after one day in culture, as assessed by double staining with calcein (green, live cells) and propidium iodide (red, dead cells) (FIG. 11, top panels). CPCs were capable of adhering and spreading within the sulfated hydrogel networks containing the adhesive ligand bspRGD(15), as assessed by double staining for f-actin stress fibers (TRITC-phalloidin, red) and nuclei (DAPI, blue) (FIG. 11, bottom panels).

Figure 12:
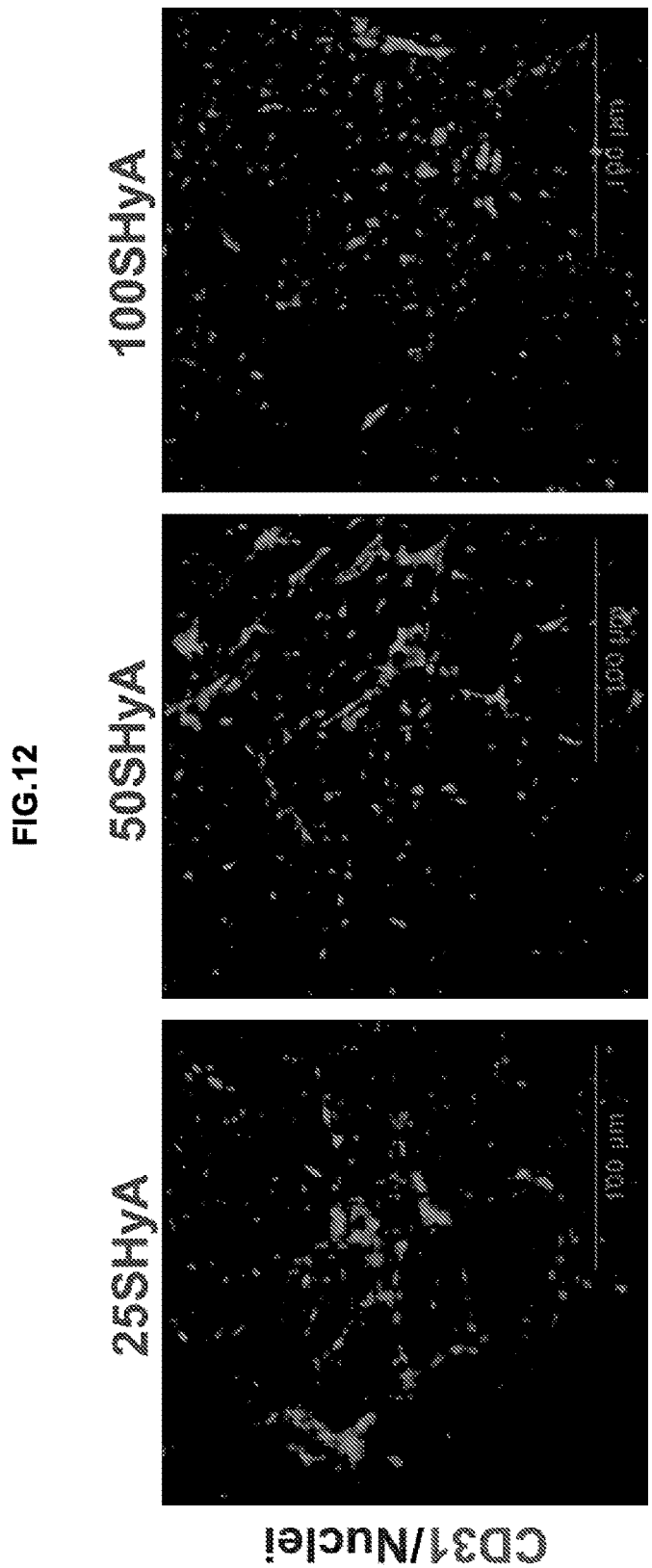
FIG. 12 depicts the effects of sulfation of hyaluronic acid on cell differentiation.

CPC differentiation was also assessed in sulfated hyaluronic acid (SHyA) with varied degrees of sulfation. CPCs encapsulated in sulfated hydrogels containing bspRGD(15) and TGFβ1 were stained for the endothelial cell marker CD31 using immunohistochemistry. CD31 positive cells were observed indicating in situ differentiation of CPCs to endothelial cells and vascular morphology became apparent after 12 days in culture (FIG. 12).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A sulfonated hyaluronic acid matrix comprising a sulfonated hyaluronic acid polymer comprising a sulfonate-containing moiety coupled to a reactive aldehyde group of an oxidized hyaluronic acid, wherein the sulfonate-containing moiety is selected from the group consisting of: 3-oxo-propane-1-sulfonate, 2-aminoethanesulfonate, and 2-aminoethyl hydrogen sulfate.

2. An implantable sulfonated hyaluronic acid material comprising:
   a) a sulfonated hyaluronic acid matrix according to claim 1; and
   b) a living cell and/or an active agent.

3. The implantable sulfonated hyaluronic acid material of claim 2, wherein the living cell is a stem cell, a neural cell, a neural progenitor cell, a muscle cell, a muscle progenitor cell, a skin cell, an endothelial cell, or an epithelial cell.

4. A sulfonated hyaluronic acid drug delivery composition comprising:
   a) a sulfonated hyaluronic acid matrix according to claim 1; and
   b) an active agent associated with, embedded with, or encapsulated within, the sulfonated hyaluronic acid matrix.

5. The sulfonated hyaluronic acid matrix of claim 1, wherein the sulfonated hyaluronic acid polymer has a sulfonate:disaccharide ratio of 1 or less.

6. The sulfonated hyaluronic acid matrix of claim 1, wherein the sulfonated hyaluronic acid polymer has a sulfonate:disaccharide ratio of 0.5 or less.

7. The sulfonated hyaluronic acid matrix of claim 1, wherein the sulfonated hyaluronic acid polymer has a sulfonate:disaccharide ratio of 0.1 or less.

8. The sulfonated hyaluronic acid matrix of claim 1, wherein the sulfonated hyaluronic acid polymer has an in vivo half-life of 8 hours or more.

9. The sulfonated hyaluronic acid matrix of claim 1, wherein the sulfonated hyaluronic acid polymer has an in vivo half-life of 10 hours or more.

10. The sulfonated hyaluronic acid matrix of claim 1, wherein the sulfonated hyaluronic acid polymer has an in vivo half-life of 12 hours or more.

11. The sulfonated hyaluronic acid matrix of claim 1, wherein the sulfonated hyaluronic acid polymer has a molecular weight of 100 kDa or more.

12. The sulfonated hyaluronic acid matrix of claim 1, wherein the sulfonated hyaluronic acid polymer has a molecular weight of 400 kDa or more.

13. The sulfonated hyaluronic acid matrix of claim 1, wherein the sulfonated hyaluronic acid polymer has a molecular weight of 800 kDa or more.

14. The sulfonated hyaluronic acid matrix of claim 1, comprising one or more additional moieties selected from a crosslinker, a polypeptide, a label, and a drug.

15. The sulfonated hyaluronic acid matrix of claim 1, comprising a polypeptide conjugated to the sulfonated hyaluronic acid polymer.

16. The sulfonated hyaluronic acid matrix of claim 15, wherein the polypeptide has a molecular weight of from 1 kDa to about 2000 kDa.

17. The sulfonated hyaluronic acid matrix of claim 1, wherein the oxidized hyaluronic acid comprises a D-glucuronic acid ring that is cleaved to form two reactive aldehyde groups.

* * * * *